United States Patent [19]

Wiesenfeldt et al.

[11] Patent Number: 5,260,446
[45] Date of Patent: Nov. 9, 1993

[54] AMINOTHIAZOLES

[75] Inventors: Matthias Wiesenfeldt, Mutterstadt; Karl-Heinz Etzbach, Frankenthal; Sabine Gruettner, Mutterstadt; Helmut Reichelt, Neustadt, all of Fed. Rep. of Germany

[73] Assignee: BASF Aktiengesellschaft, Ludwigshafen, Fed. Rep. of Germany

[21] Appl. No.: 865,754

[22] Filed: Apr. 10, 1992

Related U.S. Application Data

[63] Continuation-in-part of Ser. No. 631,430, Dec. 21, 1990, abandoned.

Foreign Application Priority Data

Dec. 22, 1989 [DE] Fed. Rep. of Germany ....... 3942581
Sep. 20, 1990 [DE] Fed. Rep. of Germany ....... 4029732

[51] Int. Cl.$^5$ .......................................... C07D 277/54
[52] U.S. Cl. .................................. 548/184; 540/603; 544/60; 544/133; 544/368; 546/209
[58] Field of Search .................. 548/184; 540/603; 544/133, 368, 60; 546/209

[56] References Cited

U.S. PATENT DOCUMENTS 4,324,899 4/1982 Frishberg .

FOREIGN PATENT DOCUMENTS 160818 11/1985 European Pat. Off. .
963847 7/1950 France .

OTHER PUBLICATIONS

Tetrahedron Letters. Bd. 28, Nr. 1, 1981, Oxford GB Seiten 117-120; Robert G. Guy et al: 'Reactions of alpha-thiocyanato-beta-dicarbonyl compounds: a C-S-C+ C-N Route to thiazoles' "Insgesamt".
Tetrahedron Letters. Bd. 22, Nr. 24, 1981, Oxford GB Seiten 2285-2288; Masataka Yokohama et al: "Diaminothiazoles and Diaminothiophenes'Insgesamt".
Tetrahedron Letters, vol. 22, No. 24, pp. 2285-2288, 1981, M. Yokoyama, et al, "Diaminothiazoles and Diaminothiophenes".
Tetrahedron Letter, vol. 28, No. 1, pp. 117-120, 1987, R. G. Guy, et al., "Reactions of α-Thiocyanato-β-Dicarbonyl Compounds: A C-S-C+ C-N Route to Thiazoles".

*Primary Examiner*—Robert Gerstl
*Attorney, Agent, or Firm*—Oblon, Spivak, McClelland, Maier & Neustadt

[57] ABSTRACT

Aminothiazoles of the formula

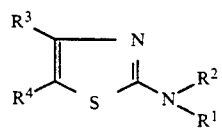

or the tautomers thereof, where $R^1$ and $R^2$ are each hydrogen or together form a radical of the formula

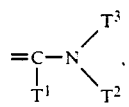

where $T^1$ is hydrogen, alkyl or phenyl, $T^2$ and $T^3$ are each, independently of one another, alkyl or phenyl, or $T^2$ and $T^3$ form, together with the nitrogen atom connecting them, a heterocyclic radical, $R^3$ is substituted mercapto or substituted amino and $R^4$ is alkanoyl, benzoyl, cyano or

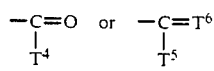

where $T^4$ is hydroxyl, $C_1$-$C_6$-alkoxy, amino or $R^3$, $T^5$ is hydrogen, alkyl or phenyl and $T^6$ is the radical of a primary amine or of an active methylene compound, are prepared as described.

2 Claims, No Drawings

AMINOTHIAZOLES

This application is a continuation-in-part of application Ser. No. 07/631,430, filed on Dec. 21, 1990, now abandoned.

The present invention relates to novel aminothiazoles of the formula I

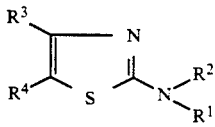

or the tautomers thereof, where $R^1$ and $R^2$ are each hydrogen or together form a radical of the formula

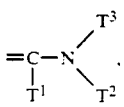

where $T^1$ is hydrogen, $C_1$–$C_6$-alkyl or phenyl and $T^2$ and $T^3$ are identical or different and each, independently of one another, is $C_1$–$C_6$-alkyl, $C_5$–$C_7$-cycloalkyl or phenyl, or $T^2$ and $T^3$ form, together with the nitrogen connecting them, a 5- to 7-membered saturated heterocyclic radical which may contain further hetero atoms, $R^3$ is $$-S(O)_n-X.$$

where n is 0, 1 or 2 and X is substituted or unsubstituted $C_1$–$C_{20}$-alkyl, $C_3$–$C_8$-cycloalkyl, substituted or unsubstituted $C_3$–$C_6$-alkenyl, substituted or unsubstituted $C_3$–$C_6$-alkynyl, substituted or unsubstituted phenyl or, if n is 0, also hydrogen, or $R_3$ is Y which means mono- or di-$C_1$–$C_{20}$-alkylamino, where the alkyl may be substituted and/or interrupted by one or more oxygen atoms, $C_3$–$C_6$-cycloalkylamino, adamantylamino, mono- or di-$C_2$–$C_{12}$-alkenylamino, $C_3$–$C_{12}$-alkynylamino, N-($C_1$–$C_5$-alkyl)-N-phenylamino, pyrrolidino, piperidino, morpholino, thiomorpholino, piperazino, N-($C_1$–$C_4$-alkyl)-piperazino, hexamethyleneimino, 1-imidazolyl, 1-pyrazolyl, substituted or unsubstituted phenylamino, pyridylamino, thienylamino, hydrazino, mono- or di-$C_1$–$C_4$-alkylhydrazino or phenylhydrazino and $R^4$ is $C_1$–$C_6$-alkanoyl, benzoyl, cyano or

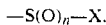

where $T^4$ is hydroxyl, $C_1$–$C_5$-alkoxy, amino or the abovementioned radical Y, $T^5$ is hydrogen, $C_1$–$C_5$-alkyl or phenyl and $T^6$ is the radical of an active methylene compound, hydroxyimino or N-Q where Q is $C_1$–$C_{20}$-alkyl which may be substituted and may be interrupted by one or more oxygen atoms, or $C_3$–$C_6$-alkenyl, $C_3$–$C_{20}$-alkynyl, $C_3$–$C_{12}$-cycloalkyl or phenyl, each of which may be substituted, pyridyl, $C_1$–$C_4$-alkoxycarbonylmethyl, amino, i-$C_1$–$C_4$-alkylamino or phenylamino, with the proviso that a) $R^3$ is not

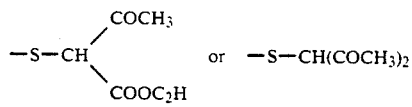

when $R^1$ and $R^2$ are each hydrogen and $R^4$ is acetyl or ethoxycarbonyl, b) $R^3$ is not methylthio when $R^1$ and $R^2$ are each hydrogen and $R^4$ is cyano, and c) $R^1$ and $R^2$ are not both hydrogen when $R^3$ is piperidino or morpholino and $R^4$ is cyano.

Tetrahedron Lett. 22 (1982) 2285–2288 has disclosed the compound 2-amino-4-methylthio-5-cyanothiazole. Furthermore, Tetrahedron Lett. 28 (1987) 117–120 describes 2-aminothiazoles which have either acetyl or ethoxycarbonyl in position 5 and

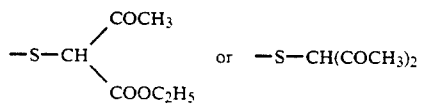

in position 4.

2,4-Diaminothiazole derivatives having a substituted amino group in position 2, a piperidino or morpholino group in position 4 and a cyano group in position 5 have also been disclosed (see, for example, Tetrahedron Lett. 22 (1981) 2285–2288).

However, these thiazoles are not especially suitable as diazo components for preparing azo dyes.

It was an object of the present invention to provide novel 2-aminothiazoles which have a mercapto group or a substituted amino group in position 4 and are intended to be especially suitable as diazo component or precursor thereof for preparing azo dyes.

We have accordingly found the aminothiazoles of the formula I defined above.

All the alkyl and alkenyl groups in the abovementioned formula I can be either straight-chain or branched.

Alkyl groups interrupted by one or more oxygen atoms in the formula I are preferably interrupted by from 1 to 3, in particular 1 to 2, oxygen atoms.

Examples of possible substituents for phenyl groups in the formula I are $C_1$–$C_6$-alkyl, $C_1$–$C_6$-alkoxy, halogen, especially fluorine, chlorine or bromine, nitro, hydroxyl, amino, mono- or di-$C_1$–$C_6$-alkylamino, acetylamino, carboxyl, carbamoyl, thiocarbamoyl, cyano, $C_1$–$C_6$-alkoxycarbonyl, trifluoromethyl, hydroxy-$C_1$–$C_3$-alkyl or $C_1$–$C_4$-alkanoyl.

Examples of possible substituents for alkyl groups in the formula I are hydroxyl, $C_1$–$C_6$-alkoxy, phenyl-$C_1$–$C_4$-alkoxy, phenoxy, amino, mono- or di-$C_1$–$C_6$-alkylamino, phenyl-$C_1$–$C_6$-alkylamino, diphenyl-$C_1$–$C_4$-alkylamino, phenylamino, diphenylamino, mono- or di-$C_3$–$C_6$-cycloalkylamino, $C_3$–$C_6$-cycloalkyl, hydroxy-$C_1$–$C_6$-alkylamino, morpholino, piperazino, N-($C_1$–$C_6$-alkyl)piperazino, thiomorpholino, piperidino, pyrrolidino, hexamethyleneimino, 2-thienyl, 2-furyl, 1H-pyrrol-2-yl, 2-pyridyl, 3-pyridyl, 4-pyridyl, phenyl, carboxyl, $C_1$–$C_3$-alkoxycarbonyl, carbamoyl, mono- or di-$C_1$–$C_4$-alkylcarbamoyl, cyano, thiocarbamoyl, phenoxycarbamoyl, phenyl-$C_1$–$C_4$-alkoxycarbonyl, mono- or diphenylcarbamoyl, mono- or di(phenyl-$C_1$–$C_4$-alkyl)carbamoyl, mono- or diphenylthiocarbamyl, mono- or di(phenyl-$C_1$-$C_4$-alkyl)thiocarbamoyl, $C_1$-$C_6$-alkylthio, phenylthio or phenyl-$C_1$-$C_4$-alkylthio.

Examples of possible substituents for alkenyl, alkynyl or cycloalkyl groups in the formula I are fluorine, chlorine or bromine.

When $T^2$ and $T^3$ form, together with the nitrogen connecting them, a 5- to 7-membered saturated heterocyclic radical which may contain further hetero atoms, possible examples are pyrrolidino, piperidino, morpholino, thiomorpholino, thiomorpholino S,S-dioxide, piperazino, N-($C_1$-$C_4$-alkyl)piperazino or hexamethyleneimino.

Examples of $T^1$, $T^2$, $T^3$ and $T^5$ are methyl, ethyl, propyl, isopropyl, butyl, isobutyl, sec-butyl, pentyl, isopentyl, neopentyl, tert-pentyl or hexyl.

Examples of $R^4$ are formyl, acetyl, propionyl, butyryl, isobutyryl, pentanoyl or hexanoyl.

(The names isooctyl, isononyl, isodecyl and isotridecyl used hereinafter are trivial names derived from the alcohols obtained by the oxo synthesis (cf. Ullmanns Encyklopädie der technischen Chemie, 4th Edition, Volume 7, pages 215 to 217 and Volume 11, pages 435 and 436.)

The radical —NQ is derived from a primary amine of the formula $H_2NX$. Examples are methylamine, ethylamine, propylamine, isopropylamine, butylamine, isobutylamine, sec-butylamine, tert-butylamine, pentylamine, isopentylamine, neopentylamine, hexylamine, heptylamine, n-octylamine, isooctylamine, 2-ethylhexylamine, nonylamine, isononylamine, decylamine, isodecylamine, undecylamine, dodecylamine, tridecylamine, isotridecylamine, tetradecylamine, pentadecylamine, hexadecylamine, heptadecylamine, octadecylamine, nonadecylamine, eicosylamine, allylamine, methallylamine, propargylamine, cyclopropylamine, cyclobutylamine, cyclopentylamine, cyclohexylamine, cycloheptylamine, cyclooctylamine, cyclononylamine, cyclodecylamine, cycloundecylamine, cyclododecylamine, 2-hydroxyethylamine, 2-methoxyethylamine, 2-ethoxyethylamine, 3-hydroxypropylamine, 3-methoxypropylamine, 3-ethoxypropylamine, 3-(2-phenoxyethoxy)propylamine, 3-benzyloxypropylamine, 2-(N,N-dimethylamino)ethylamine, 2-(N,N-diethylamino)ethylamine, 3-(N,N-dimathylamino)propylamine, 3-(N,N-diethylamino)propylamine, benzylamine, 2-phenylethylamine, 3-phenylpropylamine, aniline, 2-hydroxyaniline, 3-hydroxyaniline, 4-hydroxyaniline, o-anisidine, m-anisidine, p-anisidine, o-phenetidine, m-phenetidine, p-phenetidine, 2-chloroaniline, 3-chloroaniline, 3-nitroaniline, 4-nitroaniline, o-toluidine, m-toluidine, p-toluidine, 1,2-phenylenediamine, 1,3-phenylenediamine, 1,4-phenylenediamine, 2-trifluoromethylaniline, 3-trifluoromethylaniline, 4-trifluoromethylaniline, 2-ethylaniline, 3-ethylaniline, 4-ethylaniline, 2-aminopyridine, 3-aminopyridine, 4-aminopyridine, glycine methyl ester, glycine ethyl ester, glycine propyl ester, glycine butyl ester, hydrazine, N,N-dimethylhydrazine or phenylhydrazine.

Examples of $T^4$ are methoxy, ethoxy, propoxy, isopropoxy, butoxy, isobutoxy, sec-butoxy, pentyloxy, isopentyloxy, neopentyloxy or hexyloxy.

The radical $T^6$ is derived, for example, from an active methylene compound of the formula $H_2T^6$. Examples of formulae of these compounds are

where Z is cyano, nitro, $C_1$-$C_6$-alkanoyl, benzoyl, $C_1$-$C_4$-alkylsulfonyl, phenylsulfonyl, carboxyl, $C_1$-$C_4$-alkoxycarbonyl, carbamoyl or mono- or di-$C_1$-$C_4$-alkylcarbamoyl, or

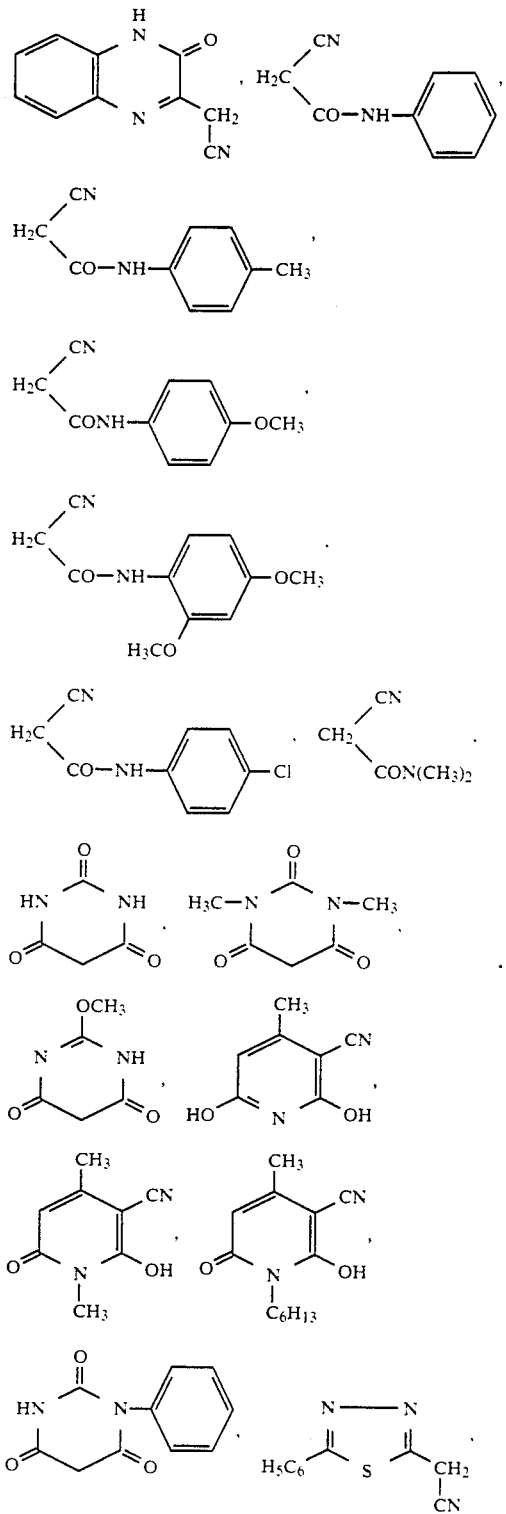

-continued

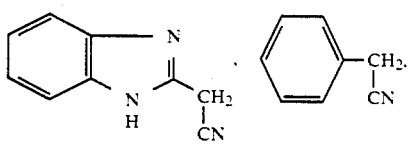
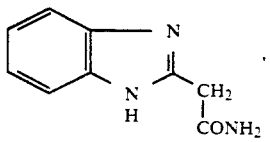
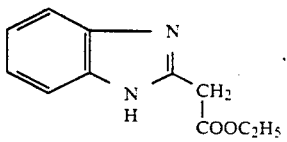
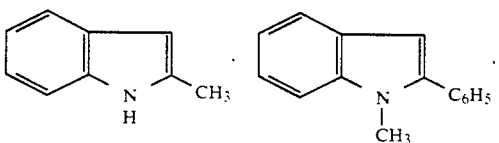
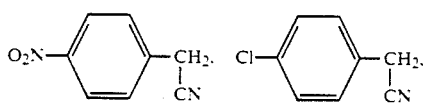
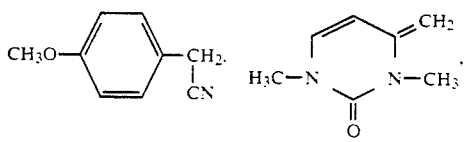
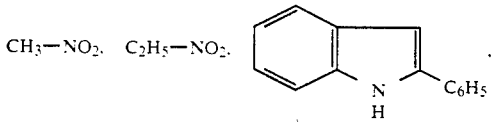
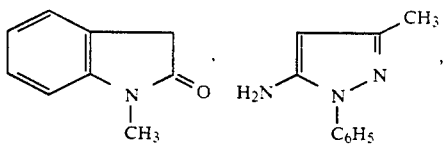
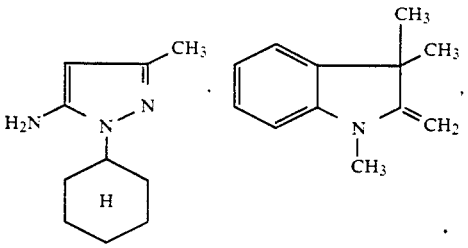
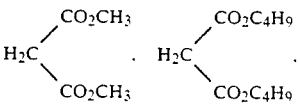

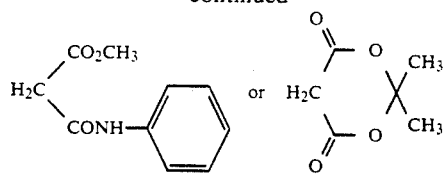

Examples of some particularly important compounds are:

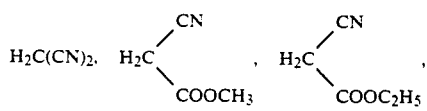
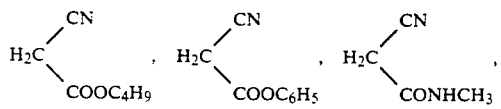
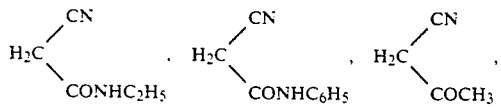
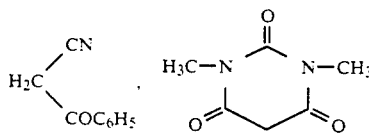
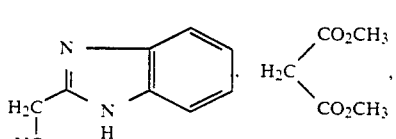
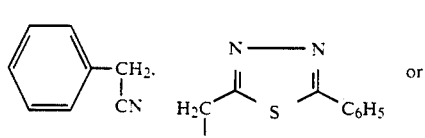
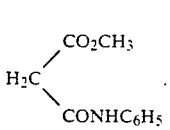

Examples of Y are methylamino, ethylamino, propylamino, isopropylamino, butylamino, isobutylamino, sec-butylamino, pentylamino, isopentylamino, neopentylamino, hexylamino, heptylamino, octylamino, isooctylamino, 2-ethylhexylamino, nonylamino, isononylamino, decylamino, isodecylamino, undecylamino, dodecylamino, tridecylamino, isotridecylamino, tetradecylamino, pentadecylamino, hexadecylamino, heptadecylamino, octadecylamino, nonadecylamino, eicosylamino, (R)-(—)-1-cyclohexylethylamino, (S)-(+)-1-cyclohexylethylamino, 2-cyclohexylethylamino, 2-hydroxyethylamino, 2-methoxyethylamino, 2-ethoxyethylamino, 2-phenoxyethylamino, 2-(2-hydroxyethoxy)ethylamino, 2-(2-hydroxyethyl)aminoethylamino, 2-aminoethylamino, 2-dimethylaminoethylamino, 2-diethylaminoethylamino, 2-diisopropylaminoethylamino, 2-(1-piperazinyl)ethylamino, 3-hydroxy-n-propylamino, -methoxy-n-propylamino, 3-ethoxy-n-propylamino, -isopropoxy-n-propylamino, 3-phenoxy-n-propylamino, 3-benzyloxy-n-propylamino, 3-(2-methoxyethoxy)-n-propylamino, 3-(2-ethoxyethoxy)-n-propylamino, 3-(2-phenoxyethoxy)-n-propylamino, 3-amino-n-propylamino, 3-dimethylamino-n-propylamino, 3-diethylamino-n-propylamino, 3-di-n-propylamino-n-propylamino, 3-diisopropylamino-n-propylamino, 3-di-n-butylamino-n-propylamino, 3-morpholino-n-propylamino, 4-hydroxy-n-butylamino, 4-amino-n-butylamino, 5-hydroxy-n-pentylamino, 5-amino-n-pentylamino, 6-hydroxy-n-hexylamino, 6-amino-n-hexylamino, 7-hydroxy-n-heptylamino, 7-amino-n-heptylamino, 8-hydroxy-n-octylamino, 8-amino-n-octylamino, 9-hydroxy-n-nonylamino, 9-amino-n-nonylamino, 10-hydroxy-n-decylamino, 10-amino-n-decylamino, 11-amino-n-undecylamino, 4-diethylamino-1-methyl-n-butylamino, 2-hydroxy-n-propylamino, 1-ethyl-2-hydroxyethylamino, 2-hydroxy-1,1-dimethylethylamino, 1,1-bis(hydroxymethyl)ethylamino, 1-ethyl-2-hydroxyethylamino, 2-carboxyethylamino, 3-carboxy-n-propylamino, 4-carboxy-n-butylamino, 5-carboxy-n-pentylamino, 10-carboxy-n-decylamino, phenylamino, o-methylphenylamino, m-methylphenylamino, p-methylphenylamino, o-ethylphenylamino, m-ethylphenylamino, p-ethylphenylamino, o-trifluoromethylphenylamino, m-trifluoromethylphenylamino, p-trifluoromethylphenylamino, o-hydroxyphenylamino, m-hydroxyphenylamino, p-hydroxyphenylamino, o-methoxyphenylamino, m-methoxyphenylamino, p-mathoxyphenylamino, o-ethoxyphenylamino, m-ethoxyphenylamino, p-ethoxyphenylamino, o-chlorophenylamino, m-chlorophenylamino, p-chlorophenylamino, o-fluorophenylamino, m-fluorophenylamino, p-fluorophenylamino, o-bromophenylamino, m-bromophenylamino, p-bromophenylamino, o-iodophenylamino, m-iodophenylamino, p-iodophenylamino, o-aminophenylamino, m-aminophenylamino, p-aminophenylamino, p-acetylaminophenylamino, o-hydroxymethylphenylamino, m-hydroxymethylphenylamino, p-hydroxymethylphenylamino, o-carboxyphenylamino, m-carboxyphenylamino, p-carboxyphenylamino, o-aminocarbonylphenylamino, m-aminocarbonylphenylamino, p-aminocarbonylphenylamino, o-cyanophenylamino, m-cyanophenylamino, p-cyanophenylamino, 2,6-dimethylphenylamino, 3,5-dimethylphenylamino, 2-hydroxy-5-methylphenylamino, 2-hydroxy-4-methylphenylamino, 4-hydroxy-2-methylphenylamino, 2-hydroxy-5-chlorophenylamino, 1-imidazolyl, 1-pyrazolyl, 2-pyridylamino, 3-pyridylamino, 4-pyridylamino, 3-pyridylmethylamino, 2-furylmethylamino, thienylamino, benzylamino, o-methoxybenzylamino, p-methoxybenzylamino, p-fluorobenzylamino, o-chlorobenzylamino, p-chlorobenzylamino, 3,4-dimethoxybenzylamino, 2-phenylethylamino, (+/−)-α-methylbenzylamino, (+)-α-methylbenzylamino, (−)-α-methylbenzylamino, 3-phenyl-n-propylamino, 1-methyl-3-phenyl-n-propylamino, cyclopropylamino, cyclobutylamino, cyclopentylamino, cyclohexylamino, cycloheptylamino, cyclooctylamino, cyclononylamino, cyclodecylamino, cyclododecylamino, allylamino, propargylamino, methallylamino, dimethylamino, diethylamino, di-n-propylamino, di-n-butylamino, diisopropylamino, diisobutylamino, di-sec-butylamino, di-n-pentylamino, diisopentylamino, di-n-hexylamino, di-(2-ethylhexyl)amino, di-n-octylamino, diallylamino, dicyclohexylamino, N-methyl-n-butylamino, N-methylcyclohexylamino, N-ethylcyclohexylamino, N-methylethanolamino, N-ethyl-1,3-dimethyl-n-propylamino, N-ethylethanolamino, N-ethyl-2-hydroxy-n-propylamino, N-tert-butylethanolamino, N-methylphenylamino, N-ethylphenylamino, N-n-propylphenylamino, N-isopropylphenylamino, N-n-butylphenylamino, dibenzylamino, N-methylbenzylamino, N-ethylbenzylamino, N-isopropylbenzylamino, N-tert-butylbenzylamino, N-(2-hydroxyethyl)benzylamino, N-phenylbenzylamino, N-benzyl-2-phenylethylamino, pyrrolidino, piperidino, hexamethyleneimino, morpholino, N-methylpiperazino, piperazino, N-ethylpiperazino or thiomorpholino.

Examples of $R^3$ are mercapto, methylthio, ethylthio, propylthio, isopropylthio, butylthio, isobutylthio, sec-butylthio, pentylthio, isopentylthio, neopentylthio, tert-pentylthio, hexylthio, heptylthio, octylthio, 2-ethylhexylthio, benzylthio, 1- or 2-phenylethylthio, cyclopentylthio, cyclohexylthio, cycloheptylthio, allylthio, methallylthio, propargylthio, phenylthio, methylsulfinyl, ethylsulfinyl, propylsulfinyl, isopropylsulfinyl, butylsulfinyl, isobutylsulfinyl, sec-butylsulfinyl, pentylsulfinyl, isopentylsulfinyl, neopentylsulfinyl, tert-pentylsulfinyl, hexylsulfinyl, heptylsulfinyl, octylsulfinyl, 2-ethylhexylsulfinyl, benzylsulfinyl, 1- or 2-phenylethylsulfinyl, cyclopentylsulfinyl, cyclohexylsulfinyl, cycloheptylsulfinyl, allylsulfinyl, methallylsulfinyl, propargylsulfinyl, phenylsulfinyl, methylsulfonyl, ethylsulfonyl, propylsulfonyl, isopropylsulfonyl, butylsulfonyl, isobutylsulfonyl, sec-butylsulfonyl, pentylsulfonyl, isopentylsulfonyl, neopentylsulfonyl, tert-pentylsulfonyl, hexylsulfonyl, heptylsulfonyl, octylsulfonyl, 2-ethylhexylsulfonyl, benzylsulfonyl, 1- or 2-phenylethylsulfonyl, cyclopentylsulfonyl, cyclohexylsulfonyl, cycloheptylsulfonyl, allylsulfonyl, methallylsulfonyl, propargylsulfonyl or phenylsulfonyl.

Preferred aminothiazoles of the formula I are those in which $R^1$ and $R^2$ are each hydrogen or together form the radical

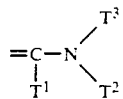

where $T^1$ is hydrogen, $C_1$-$C_4$-alkyl or phenyl and $T^2$ and $T^3$ are each, independently of one another, $C_1$-$C_4$-alkyl or phenyl, or form, together with the nitrogen atom connecting them, pyrrolidino, piperidino, morpholino, thiomorpholino, piperazino, N-($C_1$-$C_4$-alkyl)-piperazino or hexamethyleneimino, and $R^3$ and $R^4$ each has the abovementioned meanings.

Particularly preferred aminothiazoles of the formula I are those in which $R^1$ and $R^2$ are each hydrogen or together form the radical

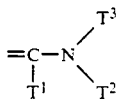

where $T^1$ is hydrogen and $T^2$ and $T^3$ are each, independently of one another, $C_1$-$C_4$-alkyl.

Further particularly preferred aminothiazoles of the formula I are those in which $R^4$ is formyl, acetyl, propionyl, butyryl, benzoyl, cyano or

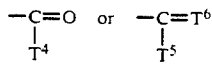

where $T^5$ is hydrogen, methyl, ethyl or phenyl, and $T^4$ and $T^6$ each has the abovementioned meanings.

Further particularly preferred aminothiazoles of the formula I are those in which Y is mono- or di-$C_1$-$C_6$-alkylamino, allylamino, methallylamino, propargylamino, $C_2$-$C_6$-alkylamino which is substituted by phenyl, hydroxyl, phenoxy, amino or mono- or di-$C_1$-$C_4$-alkylamino or interrupted by an oxygen atom, or phenylamino, pyrrolidino, piperidino, morpholino, piperazino or N-($C_1$-$C_4$-alkyl)piperazino.

Further particularly preferred aminothiazoles of the formula I are those in which $R^3$ is $C_1$-$C_6$-alkylthio, benzylthio, cyclohexylthio, $C_3$-$C_4$-alkenylthio, propargylthio, phenylthio, $C_1$-$C_6$-alkylsulfonyl, benzylsulfonyl, cyclohexylsulfonyl, $C_3$-$C_4$-alkenylsulfonyl, propargylsulfonyl or phenylsulfonyl.

Further particularly preferred aminothiazoles of the formula I are those in which $R^4$ is cyano, formyl or

where Z is cyano, nitro or $C_1$-$C_4$-alkoxycarbonyl.

Particularly important aminothiazoles of the formula I are those in which $R^1$ and $R^2$ are each hydrogen or together form the radical =CH—N(CH$_3$)$_2$.

Further particularly noteworthy aminothiazoles of the formula I are those in which $R^4$ is formyl, cyano or

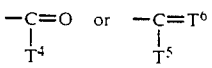

where $T^4$ is hydroxyl, methoxy, ethoxy or amino, $T^5$ is hydrogen, methyl, ethyl or phenyl and $T^6$ has the abovementioned meanings.

Attention is drawn to aminothiazoles of the formula I in which $R^4$ is formyl, cyano or

where $T^6$ has the abovementioned meanings.

Particular attention is drawn to aminothiazoles of the formula Ia

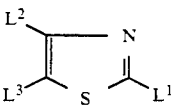

or the tautomers thereof, where
$L^1$ is amino,
$L^2$ is $C_1$-$C_6$-alkylthio, benzylthio, cyclohexylthio, $C_3$-$C_4$-alkenylthio, propargylthio, phenylthio, $C_1$-$C_6$-alkylsulfonyl, benzylsulfonyl, cyclohexylsulfonyl, $C_3$-$C_4$-alkenylsulfonyl, propargylsulfonyl, phenylsulfonyl, mono- or di-$C_1$-$C_6$-alkylamino, allylamino, methallylamino, propargylamino, $C_2$-$C_6$-alkylamino which is substituted by phenyl, hydroxyl, phenoxy, amino or mono- or di-$C_1$-$C_4$-alkylamino or interrupted by an oxygen atom, or phenylamino, pyrrolidino, piperidino, morpholino, piperazino or N-($C_1$-$C_4$-alkyl)piperazino and
$L^3$ is cyano, formyl or the radical

where Z is cyano, nitro or $C_1$-$C_4$-alkoxycarbonyl.

Particular industrial importance attaches to aminothiazoles of the formula I where n is 0 or 2 and X is benzyl or phenyl.

The aminothiazoles of the formula I according to the invention can be obtained, for example, by reacting haloaminothiazoles of the formula II

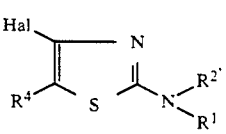

where $R^1$, $R^2$ and $R^4$ each has the abovementioned meanings, and Hal is chlorine or bromine, with a compound of the formula III

$R^3$—H     (III)

where $R^3$ has the abovementioned meanings. If $R^3$ is —S(O)$_n$—X, the compounds are generally used in the form of their alkali metal salts.

For example, the haloaminothiazole II is reacted with the compound III (or its alkali metal salt) in an inert solvent (e.g. N,N-dimethylformamide, N,N-dimethylacetamide, N-methylpyrrolidone, hexamethylphosphoric triamide, 1,3-dimethyl-2-imidazolidone, 1,3-dimethylhexahydro-2-pyrimidone, 1,2-diethoxyethane, benzene, toluene, xylene, methylene chloride, chloroform, methanol, ethanol, propanol, isopropanol, butanol or isobutanol) at from −10° to +150° C., where appropriate in the presence of a base (e.g. triethylamine, tripropylamine, tributylamine, pyridine, 4-dimethylaminopyridine, sodium methylate, sodium ethylate, potassium tert-butylate, sodium bicarbonate, sodium carbonate, potassium bicarbonate, potassium carbonate, sodium hydride or potassium hydride). The molar ratio of II:III is usually from 1:2 to 1:10. When the reaction is carried out in the presence of a base, the molar ratio of base to III is generally from 1:1 to 10:1.

The presence of a base is expedient for the reaction of compounds of the formula III where $R^3$ is —S(O)$_n$—X.

The haloaminothiazoles of the formula II are known and described, for example, in U.S. Pat. No. 4,395,544 or can be obtained by methods similar to those detailed therein.

The novel aminothiazoles are valuable intermediates for the synthesis of dyes, crop protection agents or pharmaceuticals. They are used in particular as diazo components ($R^1$, $R^2$=H) or precursors thereof for preparing azo dyes.

For preparing azo dyes the amino compound of the formula IV

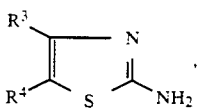         (IV)

where $R^3$ and $R^4$ have the above mentioned meanings, can for example be reacted in an acidic aqueous medium with an alkali nitrite to give a diazonium salt of the formula IVa

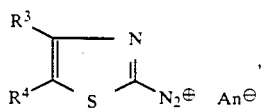         (IVa)

where $An^{\ominus}$ is an anion (e.g., chloride) and $R^3$ and $R^4$ have the abovementioned meanings, which in turn can be coupled with a coupling component of the formula V

 H—K         (V).

where K is the radical of a coupling compoent (e.g., dimethyl aniline) to yield an azo dye of the formula VI

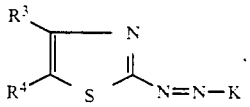         (VI)

where $R^3$, $R^4$ and K have the above meanings.

Precursors of the amino compounds IV are thiazoles of the formula IVb

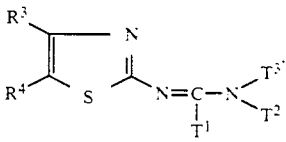         (IVb)

where $R^3$, $R^4$, $T^1$, $T^2$ and $T^3$ have the above meanings, which are easily converted to the amino compound by hydrolysis.

The Examples which follow are intended to illustrate the invention in detail.

EXAMPLE 1

3.7 g of sodium ethanolate were dissolved in 40 ml of ethanol. To this were added 4.5 g of n-butanethiol, and the mixture was stirred at room temperature for 15 minutes. Then 8.1 g of 2-amino-4-chloro-5-formylthiazole were added and the mixture was stirred at room temperature for 2 hours. The solvent was then removed by distillation under reduced pressure, and the residue was stirred with 150 ml of hot water. The suspension was adjusted to pH 3 with concentrated hydrochloric acid, cooled to 10° C. and stirred at this temperature for a further 2 hours. The precipitate was filtered off with suction, washed with water and dried in a vacuum oven at 50° C. It was purified by recrystallization from a mixture of water and acetic acid with the addition of active carbon. 8.1 g (75% of theory) of the compound of the formula

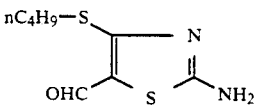

were obtained of melting point 131° to 132° C. The IR, NMR, UV and mass spectra and the elemental analysis are consistent with the indicated structure.

EXAMPLE 2

16.25 g of 2-amino-4-chloro-5-formylthiazole were dissolved in 100 ml of N,N-dimethylformamide. To this were added 19.6 g of sodium benzenesulfinate. The mixture was stirred at room temperature for one hour and at 70° C. for 4 hours. The mixture was then poured into 600 ml of ice-water, and the precipitate was filtered off with suction, washed with water and dried at 50° C. under reduced pressure. 21.6 g (81% of theory) of the compound

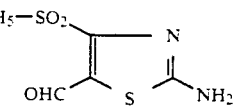

were obtained of melting point 166° to 167° C. The IR, NMR, UV and mass spectra and the elemental analysis are consistent with the indicated formula.

The compounds of the formula

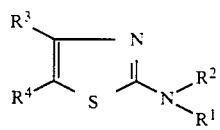

which are listed in Table 1 which follows can be prepared in a similar manner.

TABLE 1

| Example no. | $R^3$ | $NR^1R^2$ | $R^4$ | Melting point (°C.) |
|---|---|---|---|---|
| 3 | SH | $NH_2$ | CHO | |
| 4 | S—$CH_3$ | $NH_2$ | CHO | |
| 5 | S—$C_2H_5$ | $NH_2$ | CHO | |
| 6 | S-$nC_3H_7$ | $NH_2$ | CHO | 124–124.5 |
| 7 | S-$isoC_3H_7$ | $NH_2$ | CHO | |
| 8 | S-$isoC_4H_9$ | $NH_2$ | CHO | |
| 9 | S-$secC_4H_9$ | $NH_2$ | CHO | |
| 10 | S-$tertC_4H_9$ | $NH_2$ | CHO | |
| 11 | S-$nC_5H_{11}$ | $NH_2$ | CHO | |
| 12 | S-$neoC_5H_{11}$ | $NH_2$ | CHO | |
| 13 | S-$nC_6H_{13}$ | $NH_2$ | CHO | 123–125 |
| 14 | S-$nC_7H_{15}$ | $NH_2$ | CHO | |
| 15 | S-$nC_8H_{17}$ | $NH_2$ | CHO | 106–107 |

TABLE 1-continued

| Example no. | $R^3$ | $NR^1R^2$ | $R^4$ | Melting point (°C.) |
|---|---|---|---|---|
| 16 | S-nC$_9$H$_{19}$ | NH$_2$ | CHO | |
| 17 | S-nC$_{10}$H$_{21}$ | NH$_2$ | CHO | |
| 18 | S-nC$_{11}$H$_{23}$ | NH$_2$ | CHO | |
| 19 | S-nC$_{12}$H$_{25}$ | NH$_2$ | CHO | |
| 20 | S-nC$_{13}$H$_{27}$ | NH$_2$ | CHO | |
| 21 | S-nC$_{14}$H$_{29}$ | NH$_2$ | CHO | |
| 22 | S-nC$_{15}$H$_{31}$ | NH$_2$ | CHO | |
| 23 | S-nC$_{16}$H$_{33}$ | NH$_2$ | CHO | |
| 24 | S-nC$_{17}$H$_{35}$ | NH$_2$ | CHO | |
| 25 | S-nC$_{18}$H$_{37}$ | NH$_2$ | CHO | |
| 26 | S-nC$_{19}$H$_{39}$ | NH$_2$ | CHO | |
| 27 | S-nC$_{20}$H$_{41}$ | NH$_2$ | CHO | |
| 28 | S-Cyclopropyl | NH$_2$ | CHO | |
| 29 | S-Cyclopentyl | NH$_2$ | CHO | |
| 30 | S-Cyclohexyl | NH$_2$ | CHO | 162–163.5 |
| 31 | S-Cycloheptyl | NH$_2$ | CHO | |
| 32 | S-Cyclooctyl | NH$_2$ | CHO | |
| 33 | S—C$_6$H$_5$ | NH$_2$ | CHO | 174–175 |
| 34 | S—CH$_2$C$_6$H$_5$ | NH$_2$ | CHO | 153–155 |
| 35 | S—(CH$_2$)$_2$—C$_6$H$_5$ | NH$_2$ | CHO | |
| 36 | S—CH$_2$CH$_2$OH | NH$_2$ | CHO | |
| 37 | S—CH$_2$—CH=CH$_2$ | NH$_2$ | CHO | |
| 38 | S—CH$_2$—C≡CH | NH$_2$ | CHO | |
| 39 | SH | NH$_2$ | CN | |
| 40 | S—C$_2$H$_5$ | NH$_2$ | CN | |
| 41 | S-nC$_3$H$_7$ | NH$_2$ | CN | |
| 42 | S-isoC$_3$H$_7$ | NH$_2$ | CN | |
| 43 | S-nC$_4$H$_9$ | NH$_2$ | CN | |
| 44 | S-isoC$_4$H$_9$ | NH$_2$ | CN | |
| 45 | S-secC$_4$H$_9$ | NH$_2$ | CN | |
| 46 | S-tertC$_4$H$_9$ | NH$_2$ | CN | |
| 47 | S-nC$_5$H$_{11}$ | NH$_2$ | CN | |
| 48 | S-neoC$_5$H$_{11}$ | NH$_2$ | CN | |
| 49 | S-nC$_6$H$_{13}$ | NH$_2$ | CN | |
| 50 | S-nC$_7$H$_{15}$ | NH$_2$ | CN | |
| 51 | S-nC$_8$H$_{17}$ | NH$_2$ | CN | |
| 52 | S-nC$_9$H$_{19}$ | NH$_2$ | CN | |
| 53 | S-nC$_{10}$H$_{21}$ | NH$_2$ | CN | |
| 54 | S-nC$_{11}$H$_{23}$ | NH$_2$ | CN | |
| 55 | S-nC$_{12}$H$_{25}$ | NH$_2$ | CN | |
| 56 | S-nC$_{13}$H$_{25}$ | NH$_2$ | CN | |
| 57 | S-nC$_{14}$H$_{29}$ | NH$_2$ | CN | |
| 58 | S-nC$_{15}$H$_{31}$ | NH$_2$ | CN | |
| 59 | S-nC$_{16}$H$_{33}$ | NH$_2$ | CN | |
| 60 | S-nC$_{17}$H$_{35}$ | NH$_2$ | CN | |
| 61 | S-nC$_{18}$H$_{37}$ | NH$_2$ | CN | |
| 62 | S-nC$_{19}$H$_{39}$ | NH$_2$ | CN | |
| 63 | S-nC$_{20}$H$_{41}$ | NH$_2$ | CN | |
| 64 | S-Cyclopropyl | NH$_2$ | CN | |
| 65 | S-Cyclopentyl | NH$_2$ | CN | |
| 66 | S-Cyclohexyl | NH$_2$ | CN | |
| 67 | S-Cycloheptyl | NH$_2$ | CN | |
| 68 | S-Cyclooctyl | NH$_2$ | CN | |
| 69 | S—C$_6$H$_5$ | NH$_2$ | CN | |
| 70 | S—CH$_2$C$_6$H$_5$ | NH$_2$ | CN | |
| 71 | S—(CH$_2$)$_2$—C$_6$H$_5$ | NH$_2$ | CN | |
| 72 | S—CH$_2$CH$_2$OH | NH$_2$ | CN | |
| 73 | S—CH$_2$—CH=CH$_2$ | NH$_2$ | CN | |
| 74 | S—CH$_2$—C≡CH | NH$_2$ | CN | |
| 75 | S—CH$_2$—C(CH$_3$)=CH$_2$ | NH$_2$ | CHO | |
| 76 | SO$_2$—CH$_3$ | NH$_2$ | CHO | |
| 77 | SO$_2$—C$_2$H$_5$ | NH$_2$ | CHO | |
| 78 | SO$_2$-nC$_3$H$_7$ | NH$_2$ | CHO | |
| 79 | SO$_2$-isoC$_3$H$_7$ | NH$_2$ | CHO | |
| 80 | SO$_2$-nC$_4$H$_9$ | NH$_2$ | CHO | |
| 81 | SO$_2$-isoC$_4$H$_9$ | NH$_2$ | CHO | |
| 82 | SO$_2$-secC$_4$H$_9$ | NH$_2$ | CHO | |
| 83 | SO$_2$-tertC$_4$H$_9$ | NH$_2$ | CHO | |
| 84 | SO$_2$-nC$_5$H$_{11}$ | NH$_2$ | CHO | |
| 85 | SO$_2$-neoC$_5$H$_{11}$ | NH$_2$ | CHO | |
| 86 | SO$_2$-nC$_6$H$_{13}$ | NH$_2$ | CHO | |
| 87 | SO$_2$-nC$_7$H$_{15}$ | NH$_2$ | CHO | |
| 88 | SO$_2$-nC$_8$H$_{17}$ | NH$_2$ | CHO | |
| 89 | SO$_2$-nC$_9$H$_{19}$ | NH$_2$ | CHO | |
| 90 | SO$_2$-nC$_{10}$H$_{21}$ | NH$_2$ | CHO | |
| 91 | SO$_2$-nC$_{11}$H$_{23}$ | NH$_2$ | CHO | |
| 92 | SO$_2$-nC$_{12}$H$_{25}$ | NH$_2$ | CHO | |
| 93 | SO$_2$-nC$_{13}$H$_{27}$ | NH$_2$ | CHO | |

TABLE 1-continued

| Example no. | R³ | NR¹R² | R⁴ | Melting point (°C.) |
|---|---|---|---|---|
| 94 | $SO_2$-$nC_{14}H_{29}$ | $NH_2$ | CHO | |
| 95 | $SO_2$-$nC_{15}H_{31}$ | $NH_2$ | CHO | |
| 96 | $SO_2$-$nC_{16}H_{33}$ | $NH_2$ | CHO | |
| 97 | $SO_2$-$nC_{17}H_{35}$ | $NH_2$ | CHO | |
| 98 | $SO_2$-$nC_{18}H_{37}$ | $NH_2$ | CHO | |
| 99 | $SO_2$-$nC_{19}H_{39}$ | $NH_2$ | CHO | |
| 100 | $SO_2$-$nC_{20}H_{41}$ | $NH_2$ | CHO | |
| 101 | $SO_2$-Cyclopropyl | $NH_2$ | CHO | |
| 102 | $SO_2$-Cyclopentyl | $NH_2$ | CHO | |
| 103 | $SO_2$-Cyclohexyl | $NH_2$ | CHO | |
| 104 | $SO_2$-Cycloheptyl | $NH_2$ | CHO | |
| 105 | $SO_2$-Cyclooctyl | $NH_2$ | CHO | |
| 106 | $SO_2$—$C_6H_5$ | $NH_2$ | CH=C(CN) | ($COOC_2H_5$) |
| 107 | $SO_2$—$CH_2C_6H_5$ | $NH_2$ | CHO | |
| 108 | $SO_2$—$(CH_2)_2$—$C_6H_5$ | $NH_2$ | CHO | |
| 109 | $SO_2$—$CH_2CH_2OH$ | $NH_2$ | CHO | |
| 110 | $SO_2$—$CH_2$—CH=$CH_2$ | $NH_2$ | CHO | |
| 111 | $SO_2$—$CH_2$—C≡CH | $NH_2$ | CHO | |
| 112 | S—$CH_2$—C($CH_3$)=$CH_2$ | $NH_2$ | CN | |
| 113 | $SO_2$—$CH_3$ | $NH_2$ | CN | |
| 114 | $SO_2$—$C_2H_5$ | $NH_2$ | CN | |
| 115 | $SO_2$—$nC_3H_7$ | $NH_2$ | CN | |
| 116 | $SO_2$—$isoC_3H_7$ | $NH_2$ | CN | |
| 117 | $SO_2$—$nC_4H_9$ | $NH_2$ | CN | |
| 118 | $SO_2$-$isoC_4H_9$ | $NH_2$ | CN | |
| 119 | $SO_2$-$secC_4H_9$ | $NH_2$ | CN | |
| 120 | $SO_2$-$tertC_4H_9$ | $NH_2$ | CN | |
| 121 | $SO_2$-$nC_5H_{11}$ | $NH_2$ | CN | |
| 122 | $SO_2$-$neoC_5H_{11}$ | $NH_2$ | CN | |
| 123 | $SO_2$-$nC_6H_{13}$ | $NH_2$ | CN | |
| 124 | $SO_2$-$nC_7H_{15}$ | $NH_2$ | CN | |
| 125 | $SO_2$-$nC_8H_{17}$ | $NH_2$ | CN | |
| 126 | $SO_2$-$nC_9H_{19}$ | $NH_2$ | CN | |
| 127 | $SO_2$-$nC_{10}H_{21}$ | $NH_2$ | CN | |
| 128 | $SO_2$-$nC_{11}H_{23}$ | $NH_2$ | CN | |
| 129 | $SO_2$-$nC_{12}H_{25}$ | $NH_2$ | CN | |
| 130 | $SO_2$-$nC_{13}H_{27}$ | $NH_2$ | CN | |
| 131 | $SO_2$-$nC_{14}H_{29}$ | $NH_2$ | CN | |
| 132 | $SO_2$-$nC_{15}H_{31}$ | $NH_2$ | CN | |
| 133 | $SO_2$-$nC_{16}H_{33}$ | $NH_2$ | CN | |
| 134 | $SO_2$-$nC_{17}H_{35}$ | $NH_2$ | CN | |
| 135 | $SO_2$-$nC_{18}H_{37}$ | $NH_2$ | CN | |
| 136 | $SO_2$-$nC_{19}H_{39}$ | $NH_2$ | CN | |
| 137 | $SO_2$-$nC_{20}H_{41}$ | $NH_2$ | CN | |
| 138 | $SO_2$-Cyclopropyl | $NH_2$ | CN | |
| 139 | $SO_2$-Cyclopentyl | $NH_2$ | CN | |
| 140 | $SO_2$-Cyclohexyl | $NH_2$ | CN | |
| 141 | $SO_2$-Cycloheptyl | $NH_2$ | CN | |
| 142 | $SO_2$-Cyclooctyl | $NH_2$ | CN | |
| 143 | $SO_2$-$C_6H_5$ | $NH_2$ | CN | |
| 144 | $SO_2$—$CH_2C_6H_5$ | $NH_2$ | CN | |
| 145 | $SO_2$—$(CH_2)_2$—$C_6H_5$ | $NH_2$ | CN | |
| 146 | $SO_2CH_2CH_2OH$ | $NH_2$ | CN | |
| 147 | $SO_2$—$CH_2$—CH=$CH_2$ | $NH_2$ | CN | |
| 148 | $SO_2$—$CH_2$—C≡$CH_2$ | $NH_2$ | CN | |
| 149 | SH | $NH_2$ | COOH | |
| 150 | S—$CH_3$ | $NH_2$ | COOH | |
| 151 | S—$C_2H_5$ | $NH_2$ | COOH | |
| 152 | S-$nC_3H_7$ | $NH_2$ | COOH | |
| 153 | S-$isoC_3H_7$ | $NH_2$ | COOH | |
| 154 | S-$isoC_4H_9$ | $NH_2$ | COOH | |
| 155 | S-$secC_4H_9$ | $NH_2$ | COOH | |
| 156 | S-$tertC_4H_9$ | $NH_2$ | COOH | |
| 157 | S-$nC_5H_{11}$ | $NH_2$ | COOH | |
| 158 | S-$neoC_5H_{11}$ | $NH_2$ | COOH | |
| 159 | S-$nC_6H_{13}$ | $NH_2$ | COOH | |
| 160 | S-$nC_7H_{15}$ | $NH_2$ | COOH | |
| 161 | S-$nC_8H_{17}$ | $NH_2$ | COOH | |
| 162 | S-$nC_9H_{19}$ | $NH_2$ | COOH | |
| 163 | S-$nC_{10}H_{21}$ | $NH_2$ | COOH | |
| 164 | S-$nC_{11}H_{23}$ | $NH_2$ | COOH | |
| 165 | S-$nC_{12}H_{25}$ | $NH_2$ | COOH | |
| 166 | S-$nC_{13}H_{27}$ | $NH_2$ | COOH | |
| 167 | S-$nC_{14}H_{29}$ | $NH_2$ | COOH | |
| 168 | S-$nC_{15}H_{31}$ | $NH_2$ | COOH | |
| 169 | S-$nC_{16}H_{33}$ | $NH_2$ | COOH | |

TABLE 1-continued

| Example no. | $R^3$ | $NR^1R^2$ | $R^4$ | Melting point (°C.) |
|---|---|---|---|---|
| 170 | S-n$C_{17}H_{35}$ | $NH_2$ | COOH | |
| 171 | S-n$C_{18}H_{37}$ | $NH_2$ | COOH | |
| 172 | S-n$C_{20}H_{39}$ | $NH_2$ | COOH | |
| 173 | S-n$C_{20}H_{41}$ | $NH_2$ | COOH | |
| 174 | S-Cyclopropyl | $NH_2$ | COOH | |
| 175 | S-Cyclopentyl | $NH_2$ | COOH | |
| 176 | S-Cyclohexyl | $NH_2$ | COOH | |
| 177 | S-Cycloheptyl | $NH_2$ | COOH | |
| 178 | S-Cyclooctyl | $NH_2$ | COOH | |
| 179 | S—$C_6H_5$ | $NH_2$ | COOH | |
| 180 | S—$CH_2C_6H_5$ | $NH_2$ | COOH | |
| 181 | S—$(CH_2)_2$—$C_6H_5$ | $NH_2$ | COOH | |
| 182 | S—$CH_2CH_2OH$ | $NH_2$ | COOH | |
| 183 | S—$CH_2$—CH=$CH_2$ | $NH_2$ | COOH | |
| 184 | S—$CH_2$—C≡CH | $NH_2$ | COOH | |
| 185 | SH | $NH_2$ | $COOCH_3$ | |
| 186 | S—$CH_3$ | $NH_2$ | $COOCH_3$ | |
| 187 | S—$C_2H_5$ | $NH_2$ | $COOCH_3$ | |
| 188 | S-n$C_3H_7$ | $NH_2$ | $COOCH_3$ | |
| 189 | S-iso$C_3H_7$ | $NH_2$ | $COOCH_3$ | |
| 190 | S-n$C_4H_9$ | $NH_2$ | $COOCH_3$ | |
| 191 | S-iso$C_4H_9$ | $NH_2$ | $COOCH_3$ | |
| 102 | S-sec$C_4H_9$ | $NH_2$ | $COOCH_3$ | |
| 193 | S-tert$C_4H_9$ | $NH_2$ | $COOCH_3$ | |
| 194 | S-n$C_5H_{11}$ | $NH_2$ | $COOCH_3$ | |
| 195 | S-neo$C_5H_{11}$ | $NH_2$ | $COOCH_3$ | |
| 196 | S-n$C_6H_{13}$ | $NH_2$ | $COOCH_3$ | |
| 197 | S-n$C_7H_{15}$ | $NH_2$ | $COOCH_3$ | |
| 198 | S-n$C_8H_{17}$ | $NH_2$ | $COOCH_3$ | |
| 199 | S-n$C_9H_{19}$ | $NH_2$ | $COOCH_3$ | |
| 200 | S-n$C_{10}H_{21}$ | $NH_2$ | $COOCH_3$ | |
| 201 | S-n$C_{11}H_{23}$ | $NH_2$ | $COOCH_3$ | |
| 202 | S-n$C_{12}H_{25}$ | $NH_2$ | $COOCH_3$ | |
| 203 | S-n$C_{13}H_{27}$ | $NH_2$ | $COOCH_3$ | |
| 204 | S-n$C_{14}H_{29}$ | $NH_2$ | $COOCH_3$ | |
| 205 | S-n$C_{15}H_{31}$ | $NH_2$ | $COOCH_3$ | |
| 206 | S-n$C_{16}H_{33}$ | $NH_2$ | $COOCH_3$ | |
| 207 | S-n$C_{17}H_{35}$ | $NH_2$ | $COOCH_3$ | |
| 208 | S-n$C_{18}H_{37}$ | $NH_2$ | $COOCH_3$ | |
| 209 | S-n$C_{19}H_{39}$ | $NH_2$ | $COOCH_3$ | |
| 210 | S-n$C_{20}H_{41}$ | $NH_2$ | $COOCH_3$ | |
| 211 | S-Cyclopropyl | $NH_2$ | $COOCH_3$ | |
| 212 | S-Cyclopentyl | $NH_2$ | $COOCH_3$ | |
| 213 | S-Cyclohexyl | $NH_2$ | $COOCH_3$ | |
| 214 | S-Cycloheptyl | $NH_2$ | $COOCH_3$ | |
| 215 | S-Cyclooctyl | $NH_2$ | $COOCH_3$ | |
| 216 | S—$C_6H_5$ | $NH_2$ | $COOCH_3$ | |
| 217 | S—$CH_2C_6H_5$ | $NH_2$ | $COOCH_3$ | |
| 218 | S—$(CH_2)_2$—$C_6H_5$ | $NH_2$ | $COOCH_3$ | |
| 219 | S—$CH_2CH_2OH$ | $NH_2$ | $COOCH_3$ | |
| 220 | S—$CH_2$—CH=$CH_2$ | $NH_2$ | $COOCH_3$ | |
| 221 | S—$CH_2$—C≡CH | $NH_2$ | $COOCH_3$ | |
| 222 | S—$CH_2$—C($CH_3$)=$CH_2$ | $NH_2$ | COOH | |
| 223 | $SO_2$—$CH_3$ | $NH_2$ | COOH | |
| 224 | $SO_2$—$C_2H_5$ | $NH_2$ | COOH | |
| 225 | $SO_2$-n$C_3H_7$ | $NH_2$ | COOH | |
| 226 | $SO_2$-iso$C_3H_7$ | $NH_2$ | COOH | |
| 227 | $SO_2$-n$C_4H_9$ | $NH_2$ | COOH | |
| 228 | $SO_2$-iso$C_4H_9$ | $NH_2$ | COOH | |
| 229 | $SO_2$-sec$C_4H_9$ | $NH_2$ | COOH | |
| 230 | $SO_2$-tert$C_4H_9$ | $NH_2$ | COOH | |
| 231 | $SO_2$-n$C_5H_{11}$ | $NH_2$ | COOH | |
| 232 | $SO_2$-neo$C_5H_{11}$ | $NH_2$ | COOH | |
| 233 | $SO_2$-n$C_6H_{13}$ | $NH_2$ | COOH | |
| 234 | $SO_2$-n$C_7H_{15}$ | $NH_2$ | COOH | |
| 235 | $SO_2$-n$C_8H_{17}$ | $NH_2$ | COOH | |
| 236 | $SO_2$-n$C_9H_{21}$ | $NH_2$ | COOH | |
| 237 | $SO_2$-n$C_{10}H_{21}$ | $NH_2$ | COOH | |
| 238 | $SO_2$-n$C_{11}H_{23}$ | $NH_2$ | COOH | |
| 239 | $SO_2$-n$C_{12}H_{25}$ | $NH_2$ | COOH | |
| 240 | $SO_2$-n$C_{13}H_{27}$ | $NH_2$ | COOH | |
| 241 | $SO_2$-n$C_{14}H_{29}$ | $NH_2$ | COOH | |
| 242 | $SO_2$-n$C_{15}H_{31}$ | $NH_2$ | COOH | |
| 243 | $SO_2$-n$C_{16}H_{33}$ | $NH_2$ | COOH | |
| 244 | $SO_2$-n$C_{17}H_{35}$ | $NH_2$ | COOH | |
| 245 | $SO_2$-n$C_{18}H_{37}$ | $NH_2$ | COOH | |
| 246 | $SO_2$-n$C_{19}H_{39}$ | $NH_2$ | COOH | |
| 247 | $SO_2$-n$C_{20}H_{41}$ | $NH_2$ | COOH | |

TABLE 1-continued

| Example no. | $R^3$ | $NR^1R^2$ | $R^4$ | Melting point (°C.) |
|---|---|---|---|---|
| 248 | S-Cyclopropyl | $NH_2$ | COOH | |
| 249 | S-Cyclopentyl | $NH_2$ | COOH | |
| 250 | S-Cyclohexyl | $NH_2$ | COOH | |
| 251 | S-Cycloheptyl | $NH_2$ | COOH | |
| 252 | S-Cyclooctyl | $NH_2$ | COOH | |
| 253 | $SO_2$—$C_6H_5$ | $NH_2$ | COOH | |
| 254 | $SO_2$—$CH_2C_6H_5$ | $NH_2$ | COOH | |
| 255 | $SO_2$—$(CH_2)_2$—$C_6H_5$ | $NH_2$ | COOH | |
| 256 | $SO_2$—$CH_2CH_2OH$ | $NH_2$ | COOH | |
| 257 | $SO_2$—$CH_2$—$CH=CH_2$ | $NH_2$ | COOH | |
| 258 | $SO_2$—$CH_2$—$C\equiv CH$ | $NH_2$ | COOH | |
| 259 | S—$CH_2$—$C(CH_3)=CH_2$ | $NH_2$ | $COOCH_3$ | |
| 260 | $SO_2$—$CH_3$ | $NH_2$ | $COOCH_3$ | |
| 261 | $SO_2$—$C_2H_5$ | $NH_2$ | $COOCH_3$ | |
| 262 | $SO_2$-$nC_3H_7$ | $NH_2$ | $COOCH_3$ | |
| 263 | $SO_2$-iso$C_3H_7$ | $NH_2$ | $COOCH_3$ | |
| 264 | $SO_2$-$nC_4H_9$ | $NH_2$ | $COOCH_3$ | |
| 265 | $SO_2$-iso$C_4H_9$ | $NH_2$ | $COOCH_3$ | |
| 266 | $SO_2$-sec$C_4H_9$ | $NH_2$ | $COOCH_3$ | |
| 267 | $SO_2$-tert$C_4H_9$ | $NH_2$ | $COOCH_3$ | |
| 268 | $SO_2$-$nC_5H_{11}$ | $NH_2$ | $COOCH_3$ | |
| 269 | $SO_2$-neo$C_5H_{11}$ | $NH_2$ | $COOCH_3$ | |
| 270 | $SO_2$-$nC_6H_{13}$ | $NH_2$ | $COOCH_3$ | |
| 271 | $SO_2$-$nC_7H_{15}$ | $NH_2$ | $COOCH_3$ | |
| 272 | $SO_2$-$nC_8H_{17}$ | $NH_2$ | $COOCH_3$ | |
| 273 | $SO_2$-$nC_9H_{19}$ | $NH_2$ | $COOCH_3$ | |
| 274 | $SO_2$-$nC_{10}H_{21}$ | $NH_2$ | $COOCH_3$ | |
| 275 | $SO_2$-$nC_{11}H_{23}$ | $NH_2$ | $COOCH_3$ | |
| 276 | $SO_2$-$nC_{12}H_{25}$ | $NH_2$ | $COOCH_3$ | |
| 277 | $SO_2$-$nC_{13}H_{27}$ | $NH_2$ | $COOCH_3$ | |
| 278 | $SO_2$-$nC_{14}H_{29}$ | $NH_2$ | $COOCH_3$ | |
| 279 | $SO_2$-$nC_{15}H_{31}$ | $NH_2$ | $COOCH_3$ | |
| 280 | $SO_2$-$nC_{16}H_{33}$ | $NH_2$ | $COOCH_3$ | |
| 281 | $SO_2$-$nC_{17}H_{35}$ | $NH_2$ | $COOCH_3$ | |
| 282 | $SO_2$-$nC_{18}H_{37}$ | $NH_2$ | $COOCH_3$ | |
| 283 | $SO_2$-$nC_{19}H_{39}$ | $NH_2$ | $COOCH_3$ | |
| 284 | $SO_2$-$nC_{20}H_{41}$ | $NH_2$ | $COOCH_3$ | |
| 285 | S-Cyclopropyl | $NH_2$ | $COOCH_3$ | |
| 286 | S-Cyloprentyl | $NH_2$ | $COOCH_3$ | |
| 287 | S-Cyclohexyl | $NH_2$ | $COOCH_3$ | |
| 288 | S-Cycloheptyl | $NH_2$ | $COOCH_3$ | |
| 289 | S-Cyclooctyl | $NH_2$ | $COOCH_3$ | |
| 290 | $SO_2$—$C_6H_5$ | $NH_2$ | $COOCH_3$ | |
| 291 | $SO_2$—$CH_2C_6H_5$ | $NH_2$ | $COOCH_3$ | |
| 292 | $SO_2$—$(CH_2)_2$—$C_6H_5$ | $NH_2$ | $COOCH_3$ | |
| 293 | $SO_2$—$CH_2CH_2OH$ | $NH_2$ | $COOCH_3$ | |
| 294 | $SO_2$—$CH_2$—$CH=CH_2$ | $NH_2$ | $COOCH_3$ | |
| 295 | $SO_2$—$CH_2$—$CH\equiv CH$ | $NH_2$ | $COOCH_3$ | |
| 296 | S—$CH_2COOH$ | $NH_2$ | CHO | |
| 297 | S—$CH_2COOCH_3$ | $NH_2$ | CHO | |
| 298 | S—$CH_2COOC_2H_5$ | $NH_2$ | CHO | |
| 299 | S—$CH_2COOH$ | $NH_2$ | CN | |
| 300 | S—$CH_2COOCH_3$ | $NH_2$ | CN | |
| 301 | S—$CH_2COOC_2H_5$ | $NH_2$ | CN | |
| 302 | S—$C_2H_5$ | $NH_2$ | $CH=C(CN)_2$ | |
| 303 | S—$C_6H_5$ | $NH_2$ | $CH=C(CN)_2$ | |
| 304 | S—$CH_2C_6H_5$ | $NH_2$ | $CH=C(CN)_2$ | |
| 305 | $SO_2$—$C_6H_5$ | $NH_2$ | $CH=C(CN)_2$ | |
| 306 | S—$C_2H_5$ | $NH_2$ | $CH=C(CN)(COOCH_3)$ | |
| 307 | S—$C_6H_5$ | $NH_2$ | $CH=C(CN)(COOCH_3)$ | |
| 308 | S—$CH_2C_6H_5$ | $NH_2$ | $CH=C(CN)(COOCH_3)$ | |
| 309 | $SO_2$—$C_6H_5$ | $NH_2$ | $CH=C(CN)(COOCH_3)$ | |
| 310 | S-$nC_4H_9$ | $N=CH-N(CH_3)_2$ | CHO | |
| 311 | S—$C_6H_5$ | $N=CH-N(CH_3)_2$ | CHO | |
| 312 | S—$CH_2C_6H_5$ | $N=CH-N(CH_3)_2$ | CHO | |
| 313 | S—$C_2H_5$ | $N=CH-N(CH_3)_2$ | CHO | |
| 314 | SH | $N=CH-N(CH_3)_2$ | CHO | |
| 315 | $SO_2$—$C_6H_5$ | $N=CH-N(CH_3)_2$ | CHO | |
| 316 | S-$nC_4H_9$ | $N=CH-N(CH_3)_2$ | CN | |
| 317 | S—$C_6H_5$ | $N=CH-N(CH_3)_2$ | CN | |
| 318 | S—$CH_2C_6H_5$ | $N=CH-N(CH_3)_2$ | CN | |
| 319 | S—$C_2H_5$ | $N=CH-N(CH_3)_2$ | CN | |
| 320 | SH | $N=CH-N(CH_3)_2$ | CN | |
| 321 | $SO_2$—$C_6H_5$ | $N=CH-N(CH_3)_2$ | CN | |
| 322 | $SO_2$—$(CH_2)_3C_6H_5$ | $NH_2$ | CHO | |

TABLE 1-continued

| Example no. | $R^3$ | $NR^1R^2$ | $R^4$ | Melting point (°C.) |
|---|---|---|---|---|
| 323 | S—$(CH_2)_3C_6H_5$ | $NH_2$ | CHO | |
| 324 | S—$CH(CH_3)C_6H_5$ | $NH_2$ | CHO | |
| 325 | S—$CH(C_2H_5)C_6H_5$ | $NH_2$ | CHO | |
| 326 | S—$C(CH_3)_2C_6H_5$ | $NH_2$ | CHO | |
| 327 | $SO_2$—$(CH_2)_3C_6H_5$ | $NH_2$ | CN | |
| 328 | S—$(CH_2)_3C_6H_5$ | $NH_2$ | CN | |
| 329 | S—$CH(CH_3)C_6H_5$ | $NH_2$ | CN | |
| 330 | S—$CH(C_2H_5)C_6H_5$ | $NH_2$ | CN | |
| 331 | S—$C(CH_3)_2C_6H_5$ | $NH_2$ | CN | |
| 332 | S—$C_6H_5$ | N=CH-morpholino | CHO | |
| 333 | S—$CH_2C_6H_5$ | N=CH-pyrollidino | CHO | |
| 334 | $SO_2$—$C_6H_5$ | N=CH-piperidino | CHO | |
| 335 | S—$C_2H_5$ | N=CH-piperazino | CN | |
| 336 | S—$C_6H_5$ | N=CH-thiomorpholino | CHO | |
| 337 | S—$CH_2C_6H_5$ | N=CH-hexamethyleneimino | CN | |
| 338 | S—$C_6H_5$ | $NH_2$ | $COCH_3$ | |
| 339 | S—$C_2H_5$ | $NH_2$ | $COCH_3$ | |
| 340 | S—$nC_4H_9$ | $NH_2$ | $COCH_3$ | |
| 341 | S—$CH_2C_6H_5$ | $NH_2$ | $COCH_3$ | |
| 342 | $SO_2$—$C_6H_5$ | $NH_2$ | $COCH_3$ | |
| 343 | S—$C_6H_5$ | $NH_2$ | $CO_2C_2H_5$ | |
| 344 | S—$C_2H_5$ | $NH_2$ | $COC_2H_5$ | |
| 345 | S—$nC_4H_9$ | $NH_2$ | $COC_2H_5$ | |
| 346 | S—$CH_2C_6H_5$ | $NH_2$ | $COC_2H_5$ | |
| 347 | $SO_2$—$C_6H_5$ | $NH_2$ | $COC_2H_5$ | |
| 348 | S—$C_6H_5$ | $NH_2$ | CO-$nC_3H_7$ | |
| 349 | S—$C_2H_5$ | $NH_2$ | CO-$nC_4H_9$ | |
| 350 | S-$nC_4H_9$ | $NH_2$ | CO-$nC_5H_{11}$ | |
| 351 | S—$CH_2C_6H_5$ | $NH_2$ | CO-$nC_6H_{13}$ | |
| 352 | $SO_2$—$C_6H_5$ | $NH_2$ | CO-$nC_6H_{13}$ | |
| 353 | S—$C_6H_5$ | $NH_2$ | $COC_6H_5$ | |
| 354 | S—$C_2H_5$ | $NH_2$ | $COC_6H_5$ | |
| 355 | S-$nC_4H_9$ | $NH_2$ | $COC_6H_5$ | |
| 356 | S—$CH_2C_6H_5$ | $NH_2$ | $COC_6H_5$ | |
| 357 | $SO_2$—$C_6H_5$ | $NH_2$ | $COC_6H_5$ | |
| 358 | S—$C_2H_5$ | $NH_2$ | $COOC_2H_5$ | |
| 359 | S—$nC_4H_9$ | $NH_2$ | $COOC_2H_5$ | |
| 360 | S—$nC_6H_{13}$ | $NH_2$ | $COOC_2H_5$ | |
| 361 | S—$C_6H_5$ | $NH_2$ | $COOC_2H_5$ | |
| 362 | S—$CH_2C_6H_5$ | $NH_2$ | $COOC_2H_5$ | |
| 363 | $SO_2$—$C_6H_5$ | $NH_2$ | $COOC_2H_5$ | |
| 364 | S—$C_2H_5$ | $NH_2$ | COO-$nC_3H_7$ | |
| 365 | S—$nC_4H_9$ | $NH_2$ | COO-$nC_3H_7$ | |
| 366 | S—$nC_6H_{13}$ | $NH_2$ | COO-$nC_3H_7$ | |
| 367 | S—$C_6H_5$ | $NH_2$ | COO-$nC_3H_7$ | |
| 368 | S—$CH_2C_6H_5$ | $NH_2$ | COO-$nC_3H_7$ | |
| 369 | $SO_2$—$C_6H_5$ | $NH_2$ | COO-$nC_3H_7$ | |
| 370 | S—$C_2H_5$ | $NH_2$ | COO-$nC_4H_9$ | |
| 371 | S-$nC_4H_9$ | $NH_2$ | COO-$nC_4H_9$ | |
| 372 | S-$nC_6H_{13}$ | $NH_2$ | COO-$nC_4H_9$ | |
| 373 | S—$C_6H_5$ | $NH_2$ | COO-$nC_4H_9$ | |
| 374 | S—$CH_2C_6H_5$ | $NH_2$ | COO-$nC_4H_9$ | |
| 375 | $SO_2$—$C_6H_5$ | $NH_2$ | COO-$nC_4H_9$ | |
| 376 | S—$C_2H_5$ | $NH_2$ | COO-$nC_5H_{11}$ | |
| 377 | S-$nC_4H_9$ | $NH_2$ | COO-$nC_5H_{11}$ | |
| 378 | S-$nC_6H_{13}$ | $NH_2$ | COO-$nC_5H_{11}$ | |
| 379 | S—$C_6H_5$ | $NH_2$ | COO-$nC_5H_{11}$ | |
| 380 | S—$CH_2C_6H_5$ | $NH_2$ | COO-$nC_5H_{11}$ | |
| 381 | $SO_2$—$C_6H_5$ | $NH_2$ | COO-$nC_5H_{11}$ | |
| 382 | S—$C_2H_5$ | $NH_2$ | COO-$nC_6H_{13}$ | |
| 383 | S-$nC_4H_9$ | $NH_2$ | COO-$nC_6H_{13}$ | |
| 384 | S-$nC_6H_{13}$ | $NH_2$ | COO-$nC_6H_{13}$ | |
| 385 | S—$C_6H_5$ | $NH_2$ | COO-$nC_6H_{13}$ | |
| 386 | S—$CH_2C_6H_5$ | $NH_2$ | COO-$nC_6H_{13}$ | |
| 387 | $SO_2$—$C_6H_5$ | $NH_2$ | COO-$nC_6H_{13}$ | |
| 388 | S—$C_2H_5$ | $NH_2$ | $COOC_6H_5$ | |
| 389 | S-$nC_4H_9$ | $NH_2$ | $COOC_6H_5$ | |
| 390 | S-$nC_6H_{13}$ | $NH_2$ | $COOC_6H_5$ | |
| 391 | S-$C_6H_5$ | $NH_2$ | $COOC_6H_5$ | |
| 392 | S—$CH_2C_6H_5$ | $NH_2$ | $COOC_6H_5$ | |
| 393 | $SO_2$—$C_6H_5$ | $NH_2$ | $COOC_6H_5$ | |
| 394 | S—$C_2H_5$ | $NH_2$ | $CONH_2$ | |
| 395 | S-$nC_4H_9$ | $NH_2$ | $CONH_2$ | |
| 396 | S-$nC_6H_{13}$ | $NH_2$ | $CONH_2$ | |
| 397 | S—$C_6H_5$ | $NH_2$ | $CONH_2$ | |
| 398 | S—$CH_2C_6H_5$ | $NH_2$ | $CONH_2$ | |
| 399 | $SO_2$—$C_6H_5$ | $NH_2$ | $CONH_2$ | |

TABLE 1-continued

| Example no. | $R^3$ | $NR^1R^2$ | $R^4$ | Melting point (°C.) |
|---|---|---|---|---|
| 400 | S—C$_6$H$_5$ | NH$_2$ | C(CH$_3$)=C(CN)$_2$ | |
| 401 | SO$_2$—C$_6$H$_5$ | NH$_2$ | C(C$_6$H$_5$)=C(CN)$_2$ | |
| 402 | S—C$_2$H$_5$ | NH$_2$ | CON(CH$_3$)$_2$ | |
| 403 | S-nC$_4$H$_9$ | NH$_2$ | CON(CH$_3$)$_2$ | |
| 404 | S-nC$_6$H$_{13}$ | NH$_2$ | CON(CH$_3$)$_2$ | |
| 405 | S—C$_6$H$_5$ | NH$_2$ | CON(CH$_3$)$_2$ | |
| 406 | S—CH$_2$C$_6$H$_5$ | NH$_2$ | CON(CH$_3$)$_2$ | |
| 407 | SO$_2$—C$_6$H$_5$ | NH$_2$ | CON(CH$_3$)$_2$ | |
| 408 | S—C$_2$H$_5$ | NH$_2$ | CON(C$_2$H$_5$)$_2$ | |
| 409 | S-nC$_4$H$_9$ | NH$_2$ | CON(C$_2$H$_5$)$_2$ | |
| 410 | S-nC$_6$H$_{13}$ | NH$_2$ | CON(C$_2$H$_5$)$_2$ | |
| 411 | S—C$_6$H$_5$ | NH$_2$ | CON(C$_2$H$_5$)$_2$ | |
| 412 | S—CH$_2$C$_6$H$_5$ | NH$_2$ | CON(C$_2$H$_5$)$_2$ | |
| 413 | SO$_2$—C$_6$H$_5$ | NH$_2$ | CON(C$_2$H$_5$)$_2$ | |
| 414 | S—C$_2$H$_5$ | NH$_2$ | CON(C$_3$H$_7$)$_2$ | |
| 415 | S-nC$_4$H$_9$ | NH$_2$ | CON(C$_3$H$_7$)$_2$ | |
| 416 | S-nC$_6$H$_{13}$ | NH$_2$ | CON(C$_3$H$_7$)$_2$ | |
| 417 | S—C$_6$H$_5$ | NH$_2$ | CON(C$_3$H$_7$)$_2$ | |
| 418 | S—CH$_2$C$_6$H$_5$ | NH$_2$ | CON(C$_3$H$_7$)$_2$ | |
| 419 | SO$_2$—C$_6$H$_5$ | NH$_2$ | CON(C$_3$H$_7$)$_2$ | |
| 420 | S—C$_2$H$_5$ | NH$_2$ | CON(C$_4$H$_9$)$_2$ | |
| 421 | S-nC$_4$H$_9$ | NH$_2$ | CON(C$_5$H$_{11}$)$_2$ | |
| 422 | S-nC$_6$H$_{13}$ | NH$_2$ | CON(C$_6$H$_{11}$)$_2$ | |
| 423 | S—C$_6$H$_5$ | NH$_2$ | CON(CH$_3$)(C$_6$H$_5$) | |
| 424 | S—CH$_2$C$_6$H$_5$ | NH$_2$ | CON(C$_2$H$_5$)(C$_6$H$_5$) | |
| 425 | SO$_2$—C$_6$H$_5$ | NH$_2$ | CON(CH$_3$)(C$_2$H$_5$) | |
| 426 | S—C$_6$H$_5$ | NH$_2$ | CON(n-C$_3$H$_7$)(C$_6$H$_5$) | |
| 427 | SO$_2$—C$_6$H$_5$ | NH$_2$ | CON(n-C$_4$H$_9$)(C$_6$H$_5$) | |
| 428 | SO$_2$—C$_6$H$_5$ | NH$_2$ | CON(n-C$_6$H$_{13}$)(C$_6$H$_5$) | |
| 429 | S—C$_2$H$_5$ | NH$_2$ | CH=C(CN)(NO$_2$) | |
| 430 | S-nC$_4$H$_9$ | NH$_2$ | CH=C(CN)(NO$_2$) | |
| 431 | S-nC$_6$H$_{13}$ | NH$_2$ | CH=C(CN)(CONH$_2$) | |
| 432 | S—C$_6$H$_5$ | NH$_2$ | CH=C(CN)(CONH$_2$) | |
| 433 | S—CH$_2$C$_6$H$_5$ | NH$_2$ | CH=C(CN)(CONH$_2$) | |
| 434 | SO$_2$—C$_6$H$_5$ | NH$_2$ | CH=C(CN)(CONH$_2$) | |
| 435 | S—C$_2$H$_5$ | NH$_2$ | C(CH$_3$)=C(CN)$_2$ | |
| 436 | S-nC$_4$H$_9$ | NH$_2$ | C(CH$_3$)=C(CN)(NO$_2$) | |
| 437 | S-nC$_6$H$_{13}$ | NH$_2$ | C(C$_6$H$_5$)=C(CN)$_2$ | |
| 438 | S—C$_6$H$_5$ | NH$_2$ | C(C$_6$H$_5$)=C(CN)$_2$ | |
| 439 | S—CH$_2$C$_6$H$_5$ | NH$_2$ | C(C$_6$H$_5$)=C(CN)$_2$ | |
| 440 | SO$_2$—C$_6$H$_5$ | NH$_2$ | C(C$_6$H$_5$)=C(CN)$_2$ | |
| 441 | S—C$_6$H$_4$-p-CH$_3$ | NH$_2$ | CHO | 204.5-205 |
| 442 | S—C$_2$H$_5$ | NH$_2$ | CO-Morpholino | |
| 443 | S-nC$_4$H$_9$ | NH$_2$ | CO-Morpholino | |
| 444 | S-nC$_6$H$_{13}$ | NH$_2$ | CO-Morpholino | |
| 445 | S—C$_6$H$_5$ | NH$_2$ | CO-Morpholino | |
| 446 | S—CH$_2$C$_6$H$_5$ | NH$_2$ | CO-Morpholino | |
| 447 | SO$_2$—C$_6$H$_5$ | NH$_2$ | CO-Morpholino | |
| 448 | S—C$_2$H$_5$ | NH$_2$ | CO-Piperidino | |
| 449 | S-nC$_4$H$_9$ | NH$_2$ | CO-Piperidino | |
| 450 | S-nC$_6$H$_{13}$ | NH$_2$ | CO-Piperidino | |
| 451 | S—C$_6$H$_5$ | NH$_2$ | CO-Piperidino | |
| 452 | S—CH$_2$C$_6$H$_5$ | NH$_2$ | CO-Piperidino | |
| 453 | SO$_2$—C$_6$H$_5$ | NH$_2$ | CO-Piperidino | |
| 454 | S—C$_2$H$_5$ | NH$_2$ | CO-Pyrrolidino | |
| 455 | S-nC$_4$H$_9$ | NH$_2$ | CO-Pyrrolidino | |
| 456 | S-nC$_6$H$_{13}$ | NH$_2$ | CO-Pyrrolidino | |
| 457 | S—C$_6$H$_5$ | NH$_2$ | CO-Pyrrolidino | |
| 458 | S—CH$_2$C$_6$H$_5$ | NH$_2$ | CO-Pyrrolidino | |
| 459 | SO$_2$—C$_6$H$_5$ | NH$_2$ | CO-Pyrrolidino | |
| 460 | S—C$_2$H$_5$ | NH$_2$ | CO-Thiomorpholino | |
| 461 | S-nC$_4$H$_9$ | NH$_2$ | CO-Thiomorpholino | |
| 462 | S-nC$_6$H$_{13}$ | NH$_2$ | CO-Thiomorpholino | |
| 463 | S—C$_6$H$_5$ | NH$_2$ | CO-hexamethyleneimino | |
| 464 | S—CH$_2$C$_6$H$_5$ | NH$_2$ | CO-hexamethyleneimino | |
| 465 | SO$_2$—C$_6$H$_5$ | NH$_2$ | CO-hexamethyleneimino | |
| 466 | S—C$_2$H$_5$ | NH$_2$ | CO—(N-Methyl-piperazino) | |
| 467 | S-nC$_4$H$_9$ | NH$_2$ | CO—(N-Methyl-piperazino) | |
| 468 | S-nC$_6$H$_{13}$ | NH$_2$ | CO—(N-Ethyl-piperazino) | |
| 469 | S—C$_6$H$_5$ | NH$_2$ | CO—(N-Ethyl-piperazino) | |
| 470 | S—CH$_2$C$_6$H$_5$ | NH$_2$ | CO—(N-Ethyl-piperazino) | |
| 471 | SO$_2$—C$_6$H$_5$ | NH$_2$ | CO—(N-Ethyl-piperazino) | |
| 472 | S—C$_2$H$_5$ | NH$_2$ | COO-Cyclopropyl | |
| 473 | S-nC$_4$H$_9$ | NH$_2$ | COO-Cyclopropyl | |
| 474 | S-nC$_6$H$_{13}$ | NH$_2$ | COO-Cyclopentyl | |
| 475 | S—C$_6$H$_5$ | NH$_2$ | COO-Cyclopentyl | |
| 476 | S—CH$_2$C$_6$H$_5$ | NH$_2$ | COO-Cyclohexyl | |

TABLE 1-continued

| Example no. | R³ | NR¹R² | R⁴ | Melting point (°C.) |
|---|---|---|---|---|
| 477 | SO₂—C₆H₅ | NH₂ | COO-Cyclohexyl | |

EXAMPLE 478

8.1 g of 2-amino-4-chloro-5-formylthiazole were dissolved in 40 ml of N,N-dimethylformamide and, at 35° to 40° C., 9.9 ml of piperidine were added dropwise. The reaction mixture was then stirred at room temperature for 4 hours and subsequently poured into 150 ml of ice-water. The precipitate was filtered off with suction, washed with water and dried at 50° C. under reduced pressure. 6.3 g (60% of theory) of the compound of the formula

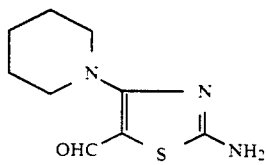

were obtained of melting point 160° C. (decomposition). The NMR, IR, UV and mass spectra and the elemental analysis are consistent with the indicated structure.

EXAMPLE 479

8 g of 2-amino-4-chloro-5-cyanothiazole were dissolved in 50 ml of N,N-dimethylformamide and, at 35° C., 7.9 ml of 70% by weight aqueous ethylamine solution were added dropwise. The reaction mixture was stirred at room temperature for 1 hour and then a further 1 ml of 70% by weight aqueous ethylamine solution was added. The reaction mixture was stirred at room temperature for a further 0.5 hour and then poured into 400 ml of ice-water and 5 ml of hydrochloric acid (M 100). The precipitate was filtered off with suction, washed with water and dried at 50° C. under reduced pressure. 4.0 g (48% of theory of the compound of the formula

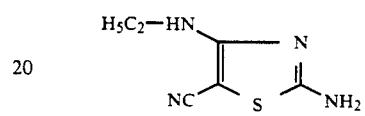

were obtained of melting point 171°–174° C. The NMR, IR, UV and mass spectra and the elemental analysis are consistent with the structure indicated above.

The compounds of the formula

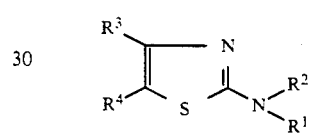

which are listed in Table 2 which follows can be prepared in a similar manner.

TABLE 2

| Example no. | R³ | NR¹R² | R⁴ | Melting point (°C.) |
|---|---|---|---|---|
| 480 | NH—CH₃ | NH₂ | CN | |
| 481 | NH-nC₃H₇ | NH₂ | CN | 121–23 |
| 482 | NH-isoC₃H₇ | NH₂ | CN | 134–36 |
| 483 | NH-nC₄H₉ | NH₂ | CN | |
| 484 | NH-secC₄H₉ | NH₂ | CN | |
| 485 | NH-isoC₄H₉ | NH₂ | CN | 203–05 |
| 486 | NH-tertC₄H₉ | NH₂ | CN | 152–53 |
| 487 | NH-nC₅H₁₁ | NH₂ | CN | |
| 488 | NH-isoC₅H₁₁ | NH₂ | CN | |
| 489 | NH—CH(CH₃)—CH(CH₃)₂ | NH₂ | CN | |
| 490 | NH-neoC₅H₁₁ | NH₂ | CN | 117–19 |
| 491 | NH-nC₆H₁₃ | NH₂ | CN | |
| 492 | NH-nC₇H₁₅ | NH₂ | CN | |
| 493 | NH-nC₈H₁₇ | NH₂ | CN | |
| 494 | NH-nC₉H₁₉ | NH₂ | CN | |
| 495 | NH-nC₁₀H₂₁ | NH₂ | CN | |
| 496 | NH-nC₁₂H₂₅ | NH₂ | CN | |
| 497 | NH-nC₁₃H₂₇ | NH₂ | CN | |
| 498 | NH-nC₁₆H₃₃ | NH₂ | CN | |
| 499 | NH-nC₁₈H₃₇ | NH₂ | CN | |
| 500 | NH—CH(CH₃)CH₂CH₂CH₃ | NH₂ | CN | |
| 501 | NH—CH(CH₃)—(CH₂)₃CH₃ | NH₂ | CN | |
| 502 | NH—CH(CH₃)—(CH₂)₂—CH(CH₃)₂ | NH₂ | CN | |
| 503 | NH—CH(CH₃)—(CH₂)₅—CH₃ | NH₂ | CN | |
| 504 | NH—CH(C₂H₅)—(CH₂)₄—CH₃ | NH₂ | CN | |
| 505 | NH—CH(CH₃)—(CH₂)₃—CH(CH₃)₂ | NH₂ | CN | |
| 506 | (R)—(−)—NH—CH(CH₃)-Cyclohexyl | NH₂ | CN | |
| 507 | (S)—(+)—NH—CH(CH₃)-Cyclohexyl | NH₂ | CN | |
| 508 | NH—CH₂CH₂-Cyclohexyl | NH₂ | CN | |
| 509 | NH—(CH₂)₂—OH | NH₂ | CN | |
| 510 | NH—(CH₂)₂—OCH₃ | NH₂ | CN | |
| 511 | NH—(CH₂)₂—OC₂H₅ | NH₂ | CN | |
| 512 | NH—(CH₂)₂—OC₆H₅ | NH₂ | CN | |
| 513 | NH—(CH₂)₂—O—(CH₂)₂OH | NH₂ | CN | |

TABLE 2-continued

| Example no. | R³ | NR¹R² | R⁴ | Melting point (°C.) |
|---|---|---|---|---|
| 514 | NH—(CH₂)₂—NH—(CH₂)₂OH | NH₂ | CN | |
| 515 | NH—(CH₂)₂—NH₂ | NH₂ | CN | |
| 516 | NH—(CH₂)₂—N(CH₃)₂ | NH₂ | CN | |
| 517 | NH—(CH₂)₂—N(C₂H₅)₂ | NH₂ | CN | |
| 518 | NH—(CH₂)₂—N(iso-C₃H₇)₂ | NH₂ | CN | |
| 519 | NH—(CH₂)₂-Piperazino | NH₂ | CN | |
| 520 | NH—(CH₂)₃OH | NH₂ | CN | |
| 521 | NH—(CH₂)₃OCH₃ | NH₂ | CN | |
| 522 | NH—(CH₂)₃OC₂H₅ | NH₂ | CN | |
| 523 | NH—(CH₂)₃—OCH(CH₃)₂ | NH₂ | CN | |
| 524 | NH—(CH₂)₃—OC₆H₅ | NH₂ | CN | |
| 525 | NH—(CH₂)₃—O—CH₂C₆H₅ | NH₂ | CN | |
| 526 | NH—(CH₂)₃—O—(CH₂)₂—O—CH₃ | NH₂ | CN | |
| 527 | NH—(CH₂)₂—O—(CH₂)₂—O—C₂H₅ | NH₂ | CN | |
| 528 | NH—(CH₂)₃—O—(CH₂)₂—O—C₆H₅ | NH₂ | CN | |
| 529 | NH—(CH₂)₃—NH₂ | NH₂ | CN | |
| 530 | NH—(CH₂)₃—N(CH₃)₂ | NH₂ | CN | |
| 531 | NH—(CH₂)₃—N(C₂H₅)₂ | NH₂ | CN | |
| 532 | NH—(CH₂)₃—N(n-C₄H₉)₂ | NH₂ | CN | |
| 533 | NH—(CH₂)₃-Morpholino | NH₂ | CN | |
| 534 | NH—(CH₂)₄—OH | NH₂ | CN | |
| 535 | NH—(CH₂)₅—NH₂ | NH₂ | CN | |
| 536 | NH—(CH₂)₆—OH | NH₂ | CN | |
| 537 | NH—(CH₂)₆—NH₂ | NH₂ | CN | |
| 538 | NH—(CH₂)₇—NH₂ | NH₂ | CN | |
| 539 | NH—(CH₂)₈—NH₂ | NH₂ | CN | |
| 540 | NH—(CH₂)₉—NH₂ | NH₂ | CN | |
| 541 | NH—(CH₂)₁₀—NH₂ | NH₂ | CN | |
| 542 | NH—(CH₂)₁₂—NH₂ | NH₂ | CN | |
| 543 | NH—CH(CH₃)—(CH₂)₃—N(C₂H₅)₂ × HCl | NH₂ | CN | |
| 544 | NH—(CH₂)—CH(CH₃)—OH | NH₂ | CN | |
| 545 | NH—CH(CH₃)—CH₂—OH | NH₂ | CN | |
| 546 | NH—CH₂-2-Thienyl | NH₂ | CN | |
| 547 | NH—C(CH₃)₂—CH₂—OH | NH₂ | CN | |
| 548 | NH—C(CH₃)—(CH₂—OH)₂ | NH₂ | CN | |
| 549 | NH—CH(C₂H₅)—CH₂—OH | NH₂ | CN | |
| 550 | NH—(CH₂)₂—COOH | NH₂ | CN | |
| 551 | NH—(CH₂)₅—COOH | NH₂ | CN | |
| 552 | NH—(CH₂)₁₀—COOH | NH₂ | CN | |
| 553 | NH—C₆H₅ | NH₂ | CN | |
| 554 | NH—C₆H₄-(2)-CH₃ | NH₂ | CN | |
| 555 | NH—C₆H₄-(3)-CH₃ | NH₂ | CN | |
| 556 | NH—C₆H₄-(4)-CH₃ | NH₂ | CN | |
| 557 | NH—C₆H₅-(2)-C₂H₅ | NH₂ | CN | |
| 558 | NH—C₆H₄-(4)-C₂H₅ | NH₂ | CN | |
| 559 | NH—C₆H₄-(2)-CF₃ | NH₂ | CN | |
| 560 | NH—C₆H₄-(3)-CF₃ | NH₂ | CN | |
| 561 | NH—C₆H₄-(4)-CF₃ | NH₂ | CN | |
| 562 | NH—C₆H₅-(2)-OH | NH₂ | CN | |
| 563 | NH—C₆H₅-(3)-OH | NH₂ | CN | |
| 564 | NH—C₆H₅-(4)-OH | NH₂ | CN | |
| 565 | NH—C₆H₄-(2)-OCH₃ | NH₂ | CN | |
| 566 | NH—C₆H₄-(3)-OCH₃ | NH₂ | CN | |
| 567 | NH—C₆H₄-(4)-OCH₃ | NH₂ | CN | |
| 568 | NH—C₆H₄-(2)-OC₂H₅ | NH₂ | CN | |
| 569 | NH—C₆H₄-(3)-OC₂H₅ | NH₂ | CN | |
| 570 | NH—C₆H₄-(4)-OC₂H₅ | NH₂ | CN | |
| 571 | NH—C₆H₄-(2)-Cl | NH₂ | CN | |
| 572 | NH—C₆H₄-(3)-Cl | NH₂ | CN | |
| 573 | NH—C₆H₄-(4)-Cl | NH₂ | CN | |
| 574 | NH—C₆H₄-(2)-F | NH₂ | CN | |
| 575 | NH—C₆H₄-(3)-F | NH₂ | CN | |
| 576 | NH—C₆H₄-(4)-F | NH₂ | CN | |
| 577 | NH—C₆H₄-(2)-Br | NH₂ | CN | |
| 578 | NH—C₆H₄-(3)-Br | NH₂ | CN | |
| 579 | NH—C₆H₄-(4)-Br | NH₂ | CN | |
| 580 | NH—C₆H₄-(2)-I | NH₂ | CN | |
| 581 | NH—C₆H₄-(3)-I | NH₂ | CN | |
| 582 | NH—C₆H₄-(4)-I | NH₂ | CN | |
| 583 | NH—C₆H₄-(2)-NH₂ | NH₂ | CN | |
| 584 | NH—C₆H₄-(3)-NH₂ | NH₂ | CN | |
| 585 | NH—C₆H₄-(4)-NH₂ | NH₂ | CN | |
| 586 | NH—C₆H₄-(4)-NH—COCH₃ | NH₂ | CN | |
| 587 | NH—C₆H₄-(2)-CH₂OH | NH₂ | CN | |
| 588 | NH—C₆H₄-(3)-CH₂OH | NH₂ | CN | |
| 589 | NH—C₆H₄-(4)-COCH₃ | NH₂ | CN | |
| 590 | NH—C₆H₄-(2)-COOH | NH₂ | CN | |
| 591 | NH—C₆H₄-(3)-COOH | NH₂ | CN | |

TABLE 2-continued

| Example no. | R³ | NR¹R² | R⁴ | Melting point (°C.) |
|---|---|---|---|---|
| 592 | NH—C₆H₄-(4)-COOH | NH₂ | CN | |
| 593 | NH—C₆H₄-(2)-CONH₂ | NH₂ | CN | |
| 594 | NH—C₆H₄-(4)-CONH₂ | NH₂ | CN | |
| 595 | NH—C₆H₄-(2)-CN | NH₂ | CN | |
| 596 | NH—C₆H₄-(3)-CN | NH₂ | CN | |
| 597 | NH—C₆H₄-(4)-CN | NH₂ | CN | |
| 598 | NH—C₆H₃-(2,6)-(CH₃)₂ | NH₂ | CN | |
| 599 | NH—C₆H₃-(3,5)-(CH₃)₂ | NH₂ | CN | |
| 600 | NH—C₆H₃-(2)-OH-(5)-CH₃ | NH₂ | CN | |
| 601 | NH—C₆H₃-(2)-OH-(4)-CH₃ | NH₂ | CN | |
| 602 | NH—C₆H₃-(2)-OH-(2)-CH₃ | NH₂ | CN | |
| 603 | NH—C₆H₃-(2)-OH-(5)-Cl | NH₂ | CN | |
| 604 | NH-2-Pyridyl | NH₂ | CN | |
| 605 | NH-3-Pyridyl | NH₂ | CN | |
| 606 | NH-4-Pyridyl | NH₂ | CN | |
| 607 | NH—CH₂-3-Pyridyl | NH₂ | CN | |
| | NH—CH₂-2-Furyl | NH₂ | CN | |
| 608 | NH—CH₂—C₆H₅ | NH₂ | CN | 119–22 |
| 609 | NH—CH₂—C₆H₄-(2)-OCH₃ | NH₂ | CN | |
| 610 | NH—CH₂—C₆H₄-(4)-OCH₃ | NH₂ | CN | |
| 611 | NH—CH₂—C₆H₄-(4)-F | NH₂ | CN | |
| 612 | NH—CH₂—C₆H₄-(2)-Cl | NH₂ | CN | |
| 613 | NH—CH₂—C₆H₄-(4)-Cl | NH₂ | CN | |
| 614 | NH—CH₂—C₆H₃-(3,4)-(OCH₃)₂ | NH₂ | CN | |
| 615 | NH—CH₂—CH₂—C₆H₅ | NH₂ | CN | |
| 616 | NH—CH(CH₃)—C₆H₅ (−/−) | NH₂ | CN | |
| 617 | NH—(CH₂)₃—C₆H₅ | NH₂ | CN | |
| 618 | NH—CH(CH₃)—(CH₂)₂—C₆H₅ | NH₂ | CN | |
| 619 | NH-Cyclopropyl | NH₂ | CN | |
| 620 | NH-Cyclopentyl | NH₂ | CN | |
| 621 | NH-Cyclohexyl | NH₂ | CN | |
| 622 | NH-Cycloheptyl | NH₂ | CN | |
| 623 | NH-Cyclooctyl | NH₂ | CN | |
| 624 | NH-Cyclododecyl | NH₂ | CN | |
| 625 | NH—CH₂—CH=CH₂ | NH₂ | CN | |
| 626 | NH—CH₂—C≡CH | NH₂ | CN | |
| 627 | N(CH₃)₂ | NH₂ | CN | |
| 628 | N(C₂H₅)₂ | NH₂ | CN | |
| 629 | N(n-C₃H₇)₂ | NH₂ | CN | |
| 630 | N(n-C₄H₉)₂ | NH₂ | CN | |
| 631 | N(iso-C₄H₉)₂ | NH₂ | CN | |
| 632 | N(n-C₅H₁₁)₂ | NH₂ | CN | |
| 633 | N(sec-C₄H₉)₂ | NH₂ | CN | |
| 634 | N(iso-C₅H₁₁)₂ | NH₂ | CN | |
| 635 | N(n-C₆H₁₃)₂ | NH₂ | CN | |
| 636 | N(CH(C₂H₅)—(CH₂)₄—CH₃)₂ | NH₂ | CN | |
| 637 | N(n-C₈H₁₇)₂ | NH₂ | CN | |
| 638 | N(CH₂—CH=CH₂)₂ | NH₂ | CN | |
| 639 | N(Cyclohexyl)₂ | NH₂ | CN | |
| 640 | N(CH₃)-nC₄H₉ | NH₂ | CN | |
| 641 | N(CH₃)-Cyclohexyl | NH₂ | CN | |
| 642 | N(C₂H₅)-Cyclohexyl | NH₂ | CN | |
| 643 | N(CH₃)—(CH₂)₂—OH | NH₂ | CN | |
| 644 | N(C₂H₅)—CH(CH₃)—CH(CH₃)₂ | NH₂ | CN | |
| 645 | N(C₂H₅)—(CH)₂—OH | NH₂ | CN | |
| 646 | N(C₂H₅)—CH₂—CH(OH)—CH₃ | NH₂ | CN | |
| 647 | N(tert-C₄H₉)—(CH₂)₂—OH | NH₂ | CN | |
| 648 | N(CH₃)—C₆H₅ | NH₂ | CN | |
| 649 | N(C₂H₅)—C₆H₅ | NH₂ | CN | |
| 650 | N(iso-C₃H₇)—C₆H₅ | NH₂ | CN | |
| 651 | N(nC₄H₉)—C₆H₅ | NH₂ | CN | |
| 652 | N(CH₂C₆H₅)₂ | NH₂ | CN | |
| 653 | N(CH₃)—CH₂C₆H₅ | NH₂ | CN | |
| 654 | N(C₂H₅)—CH₂C₆H₅ | NH₂ | CN | |
| 655 | N(iso-C₃H₇)—CH₂C₆H₅ | NH₂ | CN | |
| 656 | N(tert-C₄H₉)—CH₂C₆H₅ | NH₂ | CN | |
| 657 | N(CH₂C₆H₅)—(CH₂)₂—)OH | NH₂ | CN | |
| 658 | N(C₆H₅)—CH₂C₆H₅ | NH₂ | CN | |
| 659 | N(CH₂C₆H₅)—((CH₂)₂—C₆H₅) | NH₂ | CN | |
| 660 | Pyrrolidino | NH₂ | CN | |
| 661 | Hexamethyleneimino | NH₂ | CN | |
| 662 | N-Methylpiperazino | NH₂ | CN | |
| 663 | NH—NH₂ | NH₂ | CN | |
| 664 | NH—NH—CH₃ | NH₂ | CN | |
| 665 | NH—NH—C₆H₅ | NH₂ | CN | |
| 666 | NH—N(CH₃)₂ | NH₂ | CN | |
| 667 | NH—OH | NH₂ | CN | |
| 668 | NH—CH₃ | NH₂ | CHO | |
| 669 | NH—C₂H₅ | NH₂ | CHO | |

TABLE 2-continued

| Example | R³ | NR¹R² | R⁴ | Melting point (°C.) |
|---|---|---|---|---|
| 670 | NH-nC₃H₇ | NH₂ | CHO | |
| 671 | NH-isoC₃H₇ | NH₂ | CHO | |
| 672 | NH-secC₄H₉ | NH₂ | CHO | |
| 673 | NH-nC₅H₁₁ | NH₂ | CHO | |
| 674 | NH-Cyclohexyl | NH₂ | CHO | |
| 675 | NH—C₆H₅ | NH₂ | CHO | |
| 676 | N(C₂H₅)₂ | NH₂ | CHO | |
| 677 | NH—CH₃ | N=CH—N(CH₃)₂ | CN | |
| 678 | NH—C₂H₅ | N=CH—N(CH₃)₂ | CN | |
| 679 | NH—CH₃ | NH₂ | CH=C(CN)₂ | |
| 680 | NH—C₂H₅ | NH₂ | CH=C(CN)₂ | |
| 681 | NH-nC₃H₇ | NH₂ | CH=C(CN)₂ | |
| 682 | NH-nC₄H₉ | NH₂ | CH=C(CN)₂ | |
| 683 | NH-secC₄H₉ | NH₂ | CH=C(CN)₂ | |
| 684 | NH-nC₆H₁₃ | NH₂ | CH=C(CN)₂ | |
| 685 | NH-nC₇H₁₅ | NH₂ | CH=C(CN)₂ | |
| 686 | NH—C₂H₄—OH | NH₂ | CH=C(CN)₂ | |
| 687 | NH—C₂H₄—OCH₃ | NH₂ | CH=C(CN)₂ | |
| 688 | NH-Cyclohexyl | NH₂ | CH=C(CN)₂ | |
| 689 | NH—C₆H₅ | NH₂ | CH=C(CN)₂ | |
| 690 | NH—C₆H₄-(3)-CH₃ | NH₂ | CH=C(CN)₂ | |
| 691 | NH—CH₂—C≡CH | NH₂ | CH=C(CN)₂ | |
| 692 | NH(CH₃)₂ | NH₂ | CH=C(CN)₂ | |
| 693 | Pyrrolidino | NH₂ | CH=C(CN)₂ | |
| 694 | Piperidino | NH₂ | CH=C(CN)₂ | |
| 695 | Morpholino | NH₂ | CH=C(CN)₂ | |
| 696 | NH—NH₂ | NH₂ | CH=C(CN)₂ | |
| 697 | NH-nC₃H₇ | NH₂ | CH=C(CN) (COOCH₃) | |
| 698 | NH-nC₄H₉ | NH₂ | CH=C(CN) (COOCH₃) | |
| 699 | NH-secC₄H₉ | NH₂ | CH=C(CN) (COOCH₃) | |
| 700 | NH-nC₅H₁₁ | NH₂ | CH=C(CN) (COOC₂H₅) | |
| 701 | N(C₂H₅)₂ | NH₂ | CH=C(CN) (COOC₂H₅) | |
| 702 | NH—CH₃ | NH₂ | CH=C(CN) (NO₂) | |
| 703 | NH-isoC₃H- | NH₂ | CH=C(CN) (NO₂) | |
| 704 | (R/S)—NH—CH(CH₃)-Cyclohexyl | NH₂ | CN | |
| 705 | NH—(CH₂)₃—N(n-C₃H₇)₂ | NH₂ | CN | |
| 706 | NH—(CH₂)₃—N(iso-C₃H₇)₂ | NH₂ | CN | |
| 707 | NH—(+)—CH(CH₃)—C₆H₅ | NH₂ | CN | |
| 708 | NH—(−)—CH(CH₃)—C₆H₅ | NH₂ | CN | |
| 709 | NH-Cyclobutyl | NH₂ | CN | |
| 710 | NH-Adamantyl | NH₂ | CN | |
| 711 | NH-Cyclononyl | NH₂ | CN | |
| 712 | NH-Cyclodecyl | NH₂ | CN | |
| 713 | NH-Methallyl | NH₂ | CN | |
| 714 | N(isoC₃H₇)₂ | NH₂ | CN | |
| 715 | N-Ethylpiperazino | NH₂ | CN | |
| 716 | Thiomorpholino | NH₂ | CN | |
| 717 | NH—NH—C₂H₅ | NH₂ | CN | |
| 718 | NH—N(C₂H₅)₂ | NH₂ | CN | |
| 719 | N(CH₃)—NH—CH₃ | NH₂ | CN | |
| 720 | 1-Imidazolyl | NH₂ | CN | |
| 721 | 1-Pyrazolyl | NH₂ | CN | |
| 722 | NH—CH(CH₃)—(CH₂)₄CH₃ | NH₂ | CN | |
| 723 | Pyrrolidino | NH₂ | CHO | 174—176 |

We claim:
1. An aminothiazole of the formula I

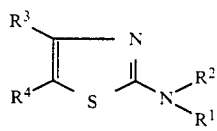

or the tautomer thereof, where
R¹ and R² are each hydrogen or together form a radical of the formula

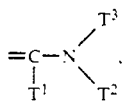

where T¹ is hydrogen, C₁–C₆-alkyl or phenyl and T² and T³ are identical or different and each, independently of one another, is C₁–C₆-alkyl, C₅–C₇-cycloalkyl or phenyl, or T² and T³ form, together with the nitrogen connecting them, a 5- to 7-membered saturated heterocyclic radical having a single hetero atom or a radical selected from the group consisting of morpholino, thiomorpholino, thiomorpholino S,S-dioxide, piperazino, N-(C₁–C₄-alkyl) piperazino and hexamethyleneimino,
R³ is

—S(O)ₙ—X, where n is 0, 1 or 2 and X is C₁–C₂₀-alkyl; C₁–C₂₀-alkyl substituted with hydroxyl, C₁–C₆-alkoxy, phenyl-C₁–C₄-alkoxy, phenoxy, amino, mono- or di-C₁–C₆-alkylamino, phenyl-C₁–C₆-alkylamino, diphenyl-C₁–C₄-alkylamino, phenylamino, diphenylamino, mono- or di-$C_3$-$C_6$-cycloalkylamino, $C_3$-$C_6$-cycloalkyl, hydroxy-$C_1$-$C_6$-alkylamino, morpholino, piperazino, N-($C_1$-$C_6$-alkyl)-piperazino, thiomorpholino, piperidino, pyrrolidino, hexamethyleneimino, 2-thienyl, 2-furyl, 1H-pyrrol-2-yl, 2-pyridyl, 3-pyridyl, 4-pyridyl, phenyl, carboxyl, $C_1$-$C_3$-alkoxycarbonyl, carbamoyl, mono- or di-$C_1$-$C_4$-alkylcarbamoyl, cyano, thiocarbamoyl, phenoxycarbamoyl, phenyl-$C_1$-$C_4$-alkoxycarbonyl, mono- or diphenylcarbamoyl, mono- or di(phenyl-$C_1$-$C_4$-alkyl)carbamoyl, mono- or diphenylthiocarbamoyl, mono- or di(phenyl-$C_1$-$C_4$-alkyl)thiocarbamoyl, $C_1$-$C_6$-alkylthio, phenylthio, phenyl-$C_1$-$C_4$-alkylthio; $C_3$-$C_8$-cycloalkyl; $C_3$-$C_8$-cycloalkyl substituted with florine, chlorine or bromine; $C_3$-$C_6$-alkenyl; $C_3$-$C_6$-alkenyl substituted with florine, chlorine or bromine; $C_3$-$C_6$-alkynyl; $C_3$-$C_6$-alkynyl substituted with florine, chlorine or bromine; phenyl; phenyl substituted with $C_1$-$C_6$-alkyl, $C_1$-$C_6$-alkoxy, halogen, nitro, hydroxyl, amino, mono- or di-$C_1$-$C_6$-alkylamino, acetyl amino, carboxyl, carbamoyl, thiocarbamoyl, cyano, $C_1$-$C_6$-alkoxy carbonyl, trifluoromethyl, hydroxy-$C_1$-$C_3$-alkyl, $C_1$-$C_4$-alkanoyl; or, if n is 0, also hydrogen, or $R_3$ is Y which means mono- or di-$C_1$-$C_{20}$-alkylamino, where the alkyl may be substituted as defined above and/or interrupted by one or more oxygen atoms, $C_3$-$C_8$-cycloalkylamino, adamantylamino, mono- or di-$C_2$-$C_{12}$-alkenylamino, $C_3$-$C_{12}$-alkynylamino, N-($C_1$-$C_5$-alkyl)-N-phenylamino, pyrrolidino, piperidino, morpholino, thiomorpholino, piperazino, N-($C_1$-$C_4$-alkyl)-piperazino, hexamethyleneimino, 1-imidazolyl, 1-pyrazolyl, phenylamino, phenylamino substituted in the ortho, meta, or para position by methyl, ethyl, trifluoromethyl, hydroxy, methoxy, ethoxy, chloro, fluoro, bromo, iodo, amino, acetyl, hydroxymethyl, carboxyphenyl, aminocabonylphenyl, cyanophenyl; or 2,6-dimethylphenylamino, 3,5-dimethylphenylamino, 2-hydroxy-5-methylphenylamino, 2-hydroxy-4-methylphenylamino, 4-hydroxy-2-methylphenylamino, 2-hydroxy-5-chlorophenylamino; 2-pyridylamino, 3-pyridylamino, 4-pyridylamino, 3-pyridylmethylamino; thienylamino, hydrazino, mono- or di-$C_1$-$C_4$-alkylhydrazino or phenylhydrazino and $R^4$ is $C_1$-$C_6$-alkanoyl, benzoyl, cyano or

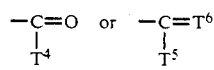

where $T^4$ is hydroxyl, $C_1$-$C_6$-alkoxy, amino or the abovementioned radical Y, $T^5$ is hydrogen, $C_1$-$C_6$-alkyl or phenyl and $T^6$ is the radical of the active methylene compound

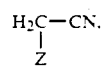

where Z is cyano, nitro, $C_1$-$C_6$-alkanoyl, benzoyl, $C_1$-$C_4$-alkylsulfonyl, phenylsulfonyl, carboxyl, $C_1$-$C_4$-alkylcarbamoyl, or $T^6$ is the radical of

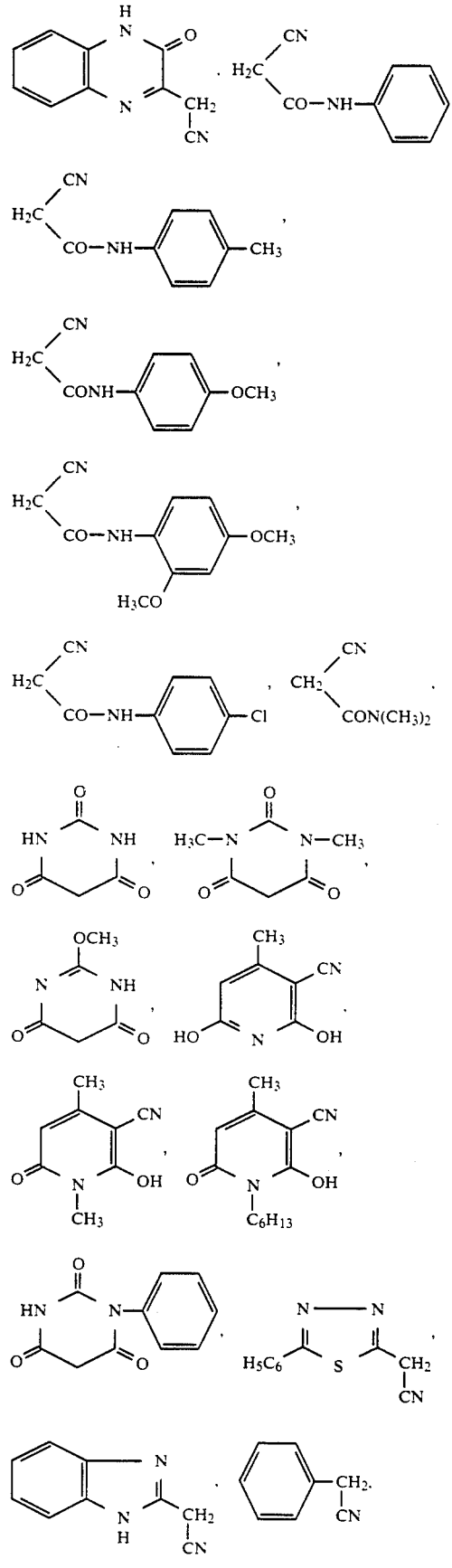

-continued

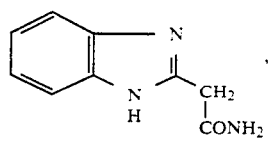

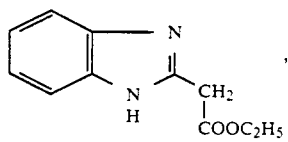

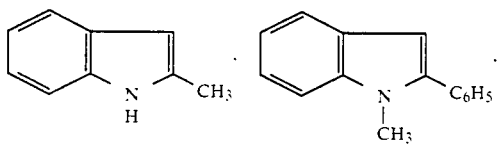

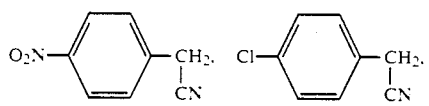

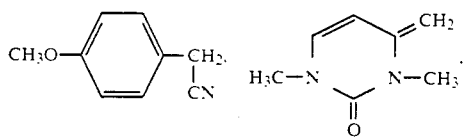

CH₃—NO₂, C₂H₅—NO₂,

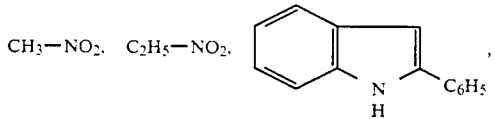

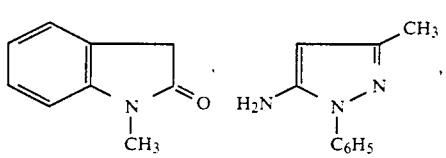

-continued

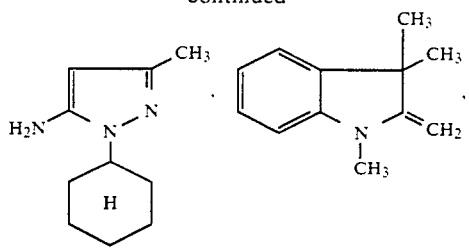

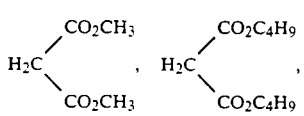

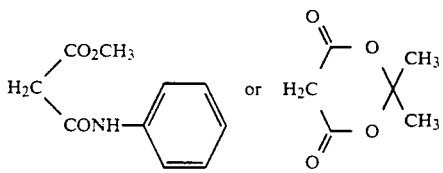

hydroxyimino or N-Q where Q is $C_1$-$C_{20}$-alkyl which may be substituted as described and may be interrupted by one or more oxygen atoms, or $C_3$-$C_6$-alkenyl, $C_3$-$C_6$-alkynyl, $C_3$-$C_{12}$-cycloalkyl or phenyl, each of which may be substituted as described above, pyridyl, $C_1$-$C_6$-alkoxycarbonylmethyl, amino, di-$C_1$-$C_4$-alkylamino or phenylamino, with the proviso that a) $R^3$ is not

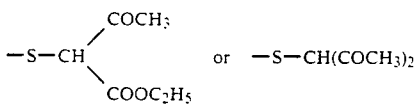

when $R^1$ and $R^2$ are each hydrogen and $R^4$ is acetyl or ethoxycarbonyl, b) $R^3$ is not methylthio when $R^1$ and $R^2$ are each hydrogen and $R^4$ is cyano, and c) $R^1$ and $R^2$ are not both hydrogen when $R^3$ is piperidino or morpholino and $R^4$ is cyano.

2. An aminothiazole as claimed in claim 1, wherein $R^1$ and $R^2$ are each hydrogen or together form the radical

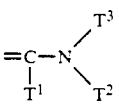

where $T^1$ is hydrogen, $C_1$-$C_4$-alkyl or phenyl and $T^2$ and $T^3$ are, independently of one another, $C_1$-$C_4$-alkyl or phenyl, or form, together with the nitrogen atom connecting them, pyrrolidino piperidino, morpholino, thiomorpholino, piperazino, N-($C_1$-$C_4$-alkyl)piperazino or hexamethyleneimino, and $R^3$ and $R^4$ each have the meanings specified in claim 1.

* * * * *